US010538787B2

(12) United States Patent
Paschon et al.

(10) Patent No.: US 10,538,787 B2
(45) Date of Patent: *Jan. 21, 2020

(54) COMPOSITIONS FOR LINKING DNA-BINDING DOMAINS AND CLEAVAGE DOMAINS

(71) Applicant: Sangamo Therapeutics, Inc., Richmond, CA (US)

(72) Inventors: David Paschon, Richmond, CA (US); Lei Zhang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 15/428,762

(22) Filed: Feb. 9, 2017

(65) Prior Publication Data

US 2017/0152527 A1 Jun. 1, 2017

Related U.S. Application Data

(63) Continuation of application No. 14/471,782, filed on Aug. 28, 2014, now Pat. No. 9,567,609.

(60) Provisional application No. 61/871,219, filed on Aug. 28, 2013.

(51) Int. Cl.
*C12N 15/90* (2006.01)
*C12N 9/22* (2006.01)
*C12N 15/01* (2006.01)
*C12N 15/62* (2006.01)

(52) U.S. Cl.
CPC ............ *C12N 15/907* (2013.01); *C12N 9/22* (2013.01); *C12N 15/01* (2013.01); *C12N 15/62* (2013.01); *C07K 2319/81* (2013.01)

(58) Field of Classification Search
CPC combination set(s) only.
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,067,317 B2 | 6/2006 | Rebar et al. |
| 7,153,949 B2 | 12/2006 | Kim et al. |
| 7,163,824 B2 | 1/2007 | Cox, III et al. |
| 7,262,054 B2 | 8/2007 | Jamieson et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,106,255 B2 | 1/2012 | Carroll et al. |
| 8,110,379 B2 | 2/2012 | DeKelver et al. |
| 8,329,986 B2 | 12/2012 | Butler et al. |
| 8,399,218 B2 | 3/2013 | Gupta et al. |
| 8,409,861 B2 | 4/2013 | Guschin et al. |
| 8,563,314 B2 | 11/2013 | Gregory et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,772,453 B2 | 7/2014 | Paschon et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0188987 A1 | 8/2006 | Guschin et al. |
| 2007/0117128 A1 | 5/2007 | Smith et al. |
| 2007/0134796 A1 | 6/2007 | Holmes et al. |
| 2008/0159996 A1 | 7/2008 | Ando et al. |
| 2008/0182332 A1 | 7/2008 | Cai et al. |
| 2009/0068164 A1 | 3/2009 | Segal et al. |
| 2009/0305419 A1 | 12/2009 | Miller |
| 2010/0218264 A1 | 8/2010 | Cui et al. |
| 2011/0201055 A1 | 8/2011 | Doyon et al. |
| 2011/0201118 A1 | 8/2011 | Yang et al. |
| 2011/0265198 A1 | 10/2011 | Gregory et al. |
| 2011/0301073 A1 | 12/2011 | Gregory et al. |

(Continued)

FOREIGN PATENT DOCUMENTS

GB 2338237 A 12/1999
WO WO 95/19431 A1 7/1995

(Continued)

OTHER PUBLICATIONS

Argast, et al., "I-PPOI and I-CREI Homing Site Sequence Degeneracy Determined by Random Mutagenesis and Sequential in Vitro Enrichment," *J. Mol. Biol.* 280:345-353 (1998).

(Continued)

*Primary Examiner* — Kagnew H Gebreyesus
(74) *Attorney, Agent, or Firm* — Pasternak Patent Law

(57) ABSTRACT

Disclosed herein are compositions for linking DNA binding domains and cleavage domains (or cleavage half-domains) to form non-naturally occurring nucleases. Also described are methods of making and using compositions comprising these linkers.

16 Claims, 21 Drawing Sheets

Specification includes a Sequence Listing.

(56) References Cited

U.S. PATENT DOCUMENTS

| | | |
|---|---|---|
| 2012/0017290 A1 | 1/2012 | Cui et al. |
| 2012/0297495 A1 | 11/2012 | McCaffrey et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2014/0335063 A1 | 11/2014 | Cannon et al. |
| 2015/0056705 A1 | 2/2015 | Conway et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 09/054985 A1 | 4/2009 |
| WO | 2009154686 A1 | 12/2009 |
| WO | WO 10/079430 A1 | 7/2010 |
| WO | WO 2014/036219 A2 | 3/2014 |

OTHER PUBLICATIONS

Ashworth, et al., "Computational Redesign of Endonuclease DNA Binding and Cleavage Specificity," *Nature* 441:656-659 (2006).

Beerli, et al., "Engineering Polydactyl Zinc-Finger Transcription Factors," *Nature Biotechnol.* 20:135-141(2002).

Belfort, et al., "Homing Endonucleases: Keeping the House in Order," *Nucleic Acids Research* 25:3379-3388 (1997).

Beurdeley, et al., "Compact Designer Talens for Efficient Genome Engineering," *Nature Communications* 4:1762 (2013) doi:10.10.38/ncomms2782.

Bibikova, et al., "Stimulation of Homologous Recombination Through Targeted Cleavage by Chimeric Nucleases," *Molecular and Cellular Biology* 21(1):289-297 (2001).

Bitinaite, et al., "Foki Dimerization is Required for DNA Cleavage," *PNAS USA* 95:10570-10575 (1998).

Boch, et al., "Breaking the Code of DNA Binding Specificity of TAL-Type III Effectors," *Science* 326:1509-1512 (2009).

Bonas, et al., "Genetic and Structural Characterization of the Avirulance Gene AVRBS3 from Xanthomonas Campestris PV. Vesicatoria," *Mol. Gen. Genet.* 218:127-136 (1989).

Chevalier, et al., "Design, Activity, and Structure of a Highly Specific Artificial Endonuclease," *Molecular Cell* 10:895-905 (2002).

Choo, et al., "Advances in Zinc Finger Engineering," *Curr. Opin. Struct. Biol.* 10:411-416 (2000).

Christian, et al., "TAL Effector Nucleases Create Targeted DNA Double-Strand Breaks," *Genetics* epub 10.1534/genetics.110.120717.

Dujon, et al., "Mobile Introns: Definition of Terms and Recommended Nomenclature," *Gene* 82:115-118 (1989).

Epinat, et al., "A Novel Engineered Meganuclease Induces Homologous Recombination in Yeast and Mammalian Cells," *Nucleic Acids Research* 31:2952-2962 (2003).

Gimble, et al., "Substrate Recognition and Induced DNA Distortion by the PI-SCEI Endonuclease, an Enzyme Generated by Protein Splicing," *J. Mol. Biol.* 263:163-180 (1996).

Guiliner, et al., "Fusion of Catalytically Inactive CAS9 to FOK1 Nuclease Improves the Specificity of Geneome Modification," *Nature Biotech* 32(6):577-582 (2014).

Guo, et al., "Directed Evolution of an Enhanced and Highly Efficient FOK1 Cleavage Domain for Zinc Finger Nucleases," *J. Mol. Biol.* 400(1):96-107 (2010).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

Handel, et al., "Expanding or Restricting the Target Site Repertoire of Zinc-Finger Nucleases: The Inter-Domain Linker as a Major Determinant of Target Site Selectivity," *Mol Ther.*17(1):104-111 (2009).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Isalan, et al., "A Rapid, Generally Applicable Method to Engineer Zinc Fingers Illustrated by Targeting the HIV-1 Promoter," *Nat. Biotechnol.* 19:656-660 (2001).

Jansen, et al., "Identification of Genes That Are Associated With DNA Repeats in Prokaryotes," *Molecular Microbiology* 43(6):1565-1575 (2002).

Jasin, et al., "Genetic Manipulation of Genomes With Rare-Cutting Endonucleases," *Trends Genet.* 12:224-228 (1996).

Kay, et al., "A Bacterial Effector Acts as a Plant Transcription Factor and Induces a Cell Size Regulator," *Science* 318:648-651 (2007).

Kim, et al., "Chimeric Restriction Endonuclease," *PNAS USA* 91:883-887 (1994).

Kim, et al., "Insertion and Deletion Mutants of FOKI Restriction Endonuclease," *J. Biol. Chem.* 269:31978-31982 (1994).

Li, et al., "Alteration of the Cleavage Distance of FOK I Restriction Endonuclease by Insertion Mutagenesis," *PNAS USA* 90:2764-2768 (1993).

Li, et al., "Functional Domains in FOK I Restriction Endonuclease," *PNAS USA* 89:4275-4279 (1992).

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).

Merutka and Stellwagen, "A Model Peptide With Enhanced Helicity," *Biochemistry* 30(17):4245-4248 (1991) doi:10.1021/bi00231a020.

Moscou, et al., "A Simple Cipher Governs DNA Recognition by TAL Effectors," *Science* 326:1501 (2009).

Pabo, et al., "Design and Selection of Novel CYS2HIS2 Zinc Finger Proteins," *Ann. Rev. Biochem.* 70:313-340 (2001).

Paques, et al., "Meganucleases and DNA Double-Strand Break-Induced Recombination: Perspectives for Gene Therapy," *Current Gene Therapy* 7:49-66 (2007).

Perler, et al., "Protein Splicing Elements: Inteins and Exteins A Definition of Terms and Recommended Nomenclature," *Nucleic Acids Research* 22:1125-1127 (1994).

Schornack, et al., "Gene-for-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Sheng, et al., "Structure-Based Cleavage Mechanism of Thermus Thermophilus Argonaute DNA Guide Strand-Mediated DNA Target Cleavage," *PNAS USA* 111(2):652-657 (2014) doi:10.1073/pnas/1321032111. (epub 2013).

Smith, et al., "Requirements for Double-Strand Cleavage by Chimeric Restriction Enzyme With Zinc Finger-DNA-Recognition Domains," *Nucleic Acids Research* 28(17):3361-3369 (2000).

Swarts, et al., "DNA-Guided DNA Interference by a Prokaryotic Argonaute," *Nature* 507(7491):258-261 (2014) doi:10.1038/nature12971.

Wah, et al., "Structure of the Multimodular Endonucleases FOK1 Bound to DNA," *Nature* 388:97-100 (1997).

Wilson, et al., "Expanding the Repertoire of Target Sites for Zinc Finger Nuclease-Mediated Genome Modification," *Mol Ther Nucleic Acids* 2(4): e88 (2013).

(56) References Cited

OTHER PUBLICATIONS

Yan, et al., "A-Helical Linker of an Artificial 6-Zinc Finger Peptide Contributes to Selective DNA Binding to a Discontinuous Recognition Sequence," *Biochemistry* 46:8517-8524 (2007).

Miller, et al., "A Tale Nuclease Architecture for Efficient Genome Editing," Nature Biotechnology, 29(2):143-148 (2011).

Lee, et al., "Emerging Tools for Synthetic Genome Design," Mol. Cells, 35(5):359-370 (2013).

Tsai, et al., "Dimeric CRISPR RNA-Guided FOKI Nucleases for Highly Specific Genome Editing," Nat. Biotechnol., 32(6):569-576 (2014).

FIGURE 1 (SEQ ID NO:1):

MDYKDHDGDYKDHDIDYKDDDDKMAPKKKRKVGIHGVPAAMAERPFQCRICMR
NFSDRSNLSRHIRTHTGEKPFACDICGRKFAISSNLNSHTKIHTGSQKPFQCRICMRNF
SRSDNLARHIRTHTGEKPFACDICGRKFATSGNLTRHTKIHLRGSQLVKSELEEKKSEL
RHKLKYVPHEYIELIEIARNSTQDRILEMKVMEFFMKVYGYRGKHLGGSRKPDGAIYT
VGSPIDYGVIVDTKAYSGGYNLPIGQADEMQRYVEENQTRNKHINPNEWWKVYPS
SVTEFKFLFVSGHFKGNYKAQLTRLNHITNCNGAVLSVEELLIGGEMIKAGTLTLEEVR
RKFNNGEINF

Figure 3

| Spacer (bp) | Sequence |
|---|---|
| 5 | cCTTTTGCAGTTTatgatAAACTGCAAAAGg ← Target sequence for CCR5 ZFN "8196"<br>gGAAAACGTCAAAactaTTTGACGTTTTCc |
| 6 | cCTTTTGCAGTTTatgcatAAACTGCAAAAGg<br>gGAAAACGTCAAAacgtaTTTGACGTTTTCc |
| 7 | cCTTTTGCAGTTTatgacatAAACTGCAAAAGg<br>gGAAAACGTCAAAactgtaTTTGACGTTTTCc |
| 8 | cCTTTTGCAGTTTatgagcatAAACTGCAAAAGg<br>gGAAAACGTCAAAactcgtaTTTGACGTTTTCc |
| 15 | cCTTTTGCAGTTTatgagtaccgatcatAAACTGCAAAAGg<br>gGAAAACGTCAAAactcatggctagtaTTTGACGTTTTCc |
| 16 | cCTTTTGCAGTTTatgagtaccgcgatcatAAACTGCAAAAGg<br>gGAAAACGTCAAAactcatgcgctagtaTTTGACGTTTTCc |

Figure 4

| 5 | 6 | 7 | 8 | 15 | 16 |
|---|---|---|---|---|---|
| TRNPGTVS | HDMPRHPF | ARPQPLHSRVHLH | QGQAVVDTPPTP | TNKRTNLS | HPPQRFGH |
| HVARRKSN | QKQPQAHR | HRDGPRNLPPTSPP | NGICPPRPRTSPP | TPAPIPTS | HSKTTNLTP |
| PSTIPYNF | NLLPPIAGS | PTRHPRAPSSAAFH | KGVHKATPPASPSY | TPNAKLPH | GATPTKLLP |
| HPPANSPTP | HPRTRSHYP | PTAQPHKAHPPHWP | TGTRSPVSTPISHP | HPIHPGIY | NRRSSPPRT |
| HPLPPIRPV | PRVLINPLV | RNTTPIPPSGPEP | TGSVHPSRPPLHNS | HPRKPVPF | HSNFQDIKEI |
| HVSHRSTPI | LSPAQSFPH | RGIQHKTQRTHPSP | PIISPLPPSAPLP | HGPRHTPV | PLFPQPELPC |
| PRPIRHPLP | VRQTKNRAE | LGSVLPSPRWLPGP | PGVAPLRPKNRVHP | GVAAASPP | SRPKYPTPHLD |
| PAARLHPAS | YTTPPPRVP | DPTSTRSSDVKFSP | PVTTYRMAHPTTP | NIRNYNAAA | GTNKYPFVAHL |
| PASPALSHT | NNSCGDSPRH | ARNGAPRPRLNILN | LGLNAFVKTPPPLP | PPPHSPPPF | GSSHDTRRPHV |
| LGKDQNRIP | KLGPLPQIPP | GSVKHRPMPHRHPA | LGLNAPVTTPPPLP | PFPYSSPHH | GARLPAGHNHT |
| TMPFARLRLT | TSSLRPHAYH | GVRRTSRLDLNAQS | TASAPAMRPVVQNA | LPARPGIPH | SLLPLAPKYHF |
| TSTLLVYRAA | HCPASRPIHP | NGMAMTQYRPLDHNP | TGKNSTSFTTRGTIP | LCCHSRPAN | SIPDLPVFSTIP |
| SYASTSCMPL | RPFLVAHTPI | NGWNHAFRPAVPSAP | TGTVHTSPICPQTYP | LPNMTLKPY | ALPPTSFPPPW |
| RTKTLPPPRP | VPNQFRDDVY | TRGLSTPRDVPTVLP | QGVLRRSFHRPPIVL | TDSKRHRSII | PSLDTPAIIPTVH |
| IPHNRPRLTVL | SLHTTSRRSI | TSPDFHPPTTNLSLP | PHITTRHSQPKTHPV x2 | RPSHFRPVPP | PHRGASSTQCLSH |
| RARQRLRSAFP | NTYYPSPPLPT | PPRPQTGEQITQPSL | PQFRAEAKPPLHNTR | FTPGHHHPHT | PSRSPASTLSPRH |
| GTHGATPTHSP | SLSATNPPFLN | PGPHTQSQTLRTPSH | AGERHRVRPTAPPTL | FSTPNTPRIN | PVAHPRPDLHPTTT |
| FDSMITAAPFI | GLQSLIPQQLL | ARAGTTPPINTLPTR | SAPVASRLLPPKSLP | SVTGSHTRDTI | AARHQNDLTSPAYS |
| TRFGIRSYPHED | VLPKPMCNPPS | ALYTQGPVRPARTPP | SSIPPRRTQVRTPTP | SLFPLRPHLPP | GTNPPNTNPRHSHY |
| SLSSQPTLVLCT | SPDLTNRSHSL | GRGLGLTLHRVPNHP | NGSQTKRFQPTHPSA x7 | KSPEAFNPIAFP | GPAKSPPNPSSTRV |
| RTLGPSCAADHT | SYLANLPYPHL | GLLYSIPNLARVSHS | PTRPSPSGLNTPVPNP | TPLLRTHVGFPR | KNSILDPRSATRAHL x2 |
| DVPNQPDRVHTT | KHHAPPIMSRPA | GFPQPHRRRAALVCP | PKLDTPTAHTPVSRTSP | SSLVMADPHYQF | PKPPPLFSSPRINNP |
| GVPPHMSHDCNT | RPAHHRPAGIPR | SGSNPTPSRVLTPIT | PNLRPSPHVNSSPPHSS | PLANSTSAHPARMPE | RVGTHPASSVRSDWP |
| NSTYSSTRPISRP | PTPTLHDAYAPS | NGHTGHRDKPAALVTR | | APACHTTPNAPRYPL | VNSDPLASAPRREPRL |
| RAQQLFAKPTHPI x2 | PTAYPSRPTFTS | TGIFRILDVSPANGSP | | GNTLFIRSEQDLVVI | SSNRPNPHATKWMPTH |
| CPGQSRNVFSTPP | PPSPPKNLNHRV | PLNAHAPKSRRTLEPP | | YHTPLNYPLLPDHYY | SQPKATTSARRPNTTT |
| TRAISRDPVNIRIH | FRSSHNPVPFTP | LRPNSLSALRSSSPLI | | HSPRRSDPPAPHSDEA | TRSTSHKARDDTRPIPC |
| SVATHPEGAATPPR | TSRSSHPVLTIPS | DPNSPISRARPLNPHP | | | RHAANPFSRHCRTAPHP |
| LINLHARNSVAYHPV | FSTGADHTPLPSA | | | | |
| | NQINPPDDTAVSKY | | | | |

Target spacer (bp)

Figure 5

Distribution of selected linker lengths

| Target Spacer (bp) | length distribution of selected linkers (aa) | | | | | | | | | |
|---|---|---|---|---|---|---|---|---|---|---|
| | 8 | 9 | 10 | 11 | 12 | 13 | 14 | 15 | 16 | 17 |
| 5 | 3 | 7 | 4 | 4 | 5 | 4 | 2 | 1 | | |
| 6 | 2 | 6 | 7 | 6 | 6 | 2 | 1 | | | |
| 7 | | | | | 1 | 1 | 10 | 12 | 5 | |
| 8 | | | | | | | 9 | 10 | 8* | 2 |
| 15 | 7 | 6 | 4 | 2 | 3 | 4 | 1 | 4 | 3 | |
| 16 | 1 | 2 | 3 | 5 | 2 | 3 | 4 | | | 2 |

\* includes 7 identical sequences

Figure 7: Linkers Selected for 8bp Dimer Gap

Figure 8

| Dimer Gap Target (bp) | Linker performance in cellular studies | |
|---|---|---|
| | # screened | # active* |
| 5 | 80 | 33 |
| 6 | 80 | 15 |
| 7 | 80 | 5 |
| 8 | 57 | 20 |
| 15 | 75 | 0 |
| 16 | 78 | 0 |

* Defined as activity ≥ that of L7a (~1/3 of L0)

Figure 9A

8bp dimer gap:

| | | | | | | | | | | | | | | | | | | | % indels |
|---|---|---|---|---|---|---|---|---|---|---|---|---|---|---|---|---|---|---|---|
| L7a | G | L | R | G | S | Q | L | V | K | S | K | S | E | A | A | A | R | (7bp gap) | 8 |
| L8a | N | G | I | C | P | P | R | P | P | T | S | P | P | A | | | | | 15 |
| L8b | T | G | T | A | P | I | E | I | P | L | A | P | S | P | | | | | 14 |
| L8c | N | G | S | Y | A | P | M | P | P | R | P | V | P | | | | | | 12 |
| L8d | P | G | I | Y | T | P | A | P | T | S | P | P | | | | | | | 12 |
| L8e | N | G | S | Q | P | P | K | P | F | R | Q | P | P | S | A | N | | | 12 |
| L8g | T | G | L | M | P | P | S | H | P | P | Q | T | P | H | I | | F | | 12 |
| L8i | T | G | T | V | H | T | S | P | P | P | Y | P | | | | | | | 11 |
| L8j | T | G | S | G | T | P | T | R | P | H | P | L | P | | | | | | 11 |

7bp dimer gap:

| | | | | | | | | | | | | | | | | | % indels |
|---|---|---|---|---|---|---|---|---|---|---|---|---|---|---|---|---|---|---|
| L7a | G | L | R | G | S | Q | L | V | K | S | K | S | E | A | A | A | R | 12 |
| L7-1 | H | L | P | P | K | P | A | N | P | F | P | L | D | P | | | | 15 |
| L7-2 | H | R | D | G | P | R | N | L | P | P | T | S | P | T | H | | | 12 |
| L7-6 | H | R | L | P | D | P | T | P | A | R | P | D | N | P | L | I | | 11 |
| L7-3 | D | P | N | S | P | I | S | R | L | C | I | H | D | S | L | F | | 15 |
| L7-5 | Y | G | P | R | P | T | P | R | P | L | P | G | S | P | | | R | 15 |
| L7-4 | G | R | P | R | R | P | D | T | P | L | G | | | | | | | 10 |

| Linker | L0 | L7a | L8a | L8c | L8d | L8g |
|---|---|---|---|---|---|---|
| # ZFNs Tested | 16 | 15 | 13 | 12 | 13 | 13 |
| # > 1% (fraction) | 9 (0.56) | 11 (0.73) | 9 (0.69) | 10 (0.83) | 10 (0.77) | 9 (0.69) |
| # > 10% (fraction) | 5 (0.31) | 7 (0.47) | 5 (0.38) | 5 (0.42) | 6 (0.46) | 6 (0.46) |
| Average Activity | 6.5 | 10.2 | 9.5 | 12.1 | 8.8 | 11.1 |

Figure 11B

8 bp gap

| ZFN Pair A | |
|---|---|
| group | %NHEJ |
| 1 | 5.2 |
| 2 | 6.2 |
| 3 | 0.0 |
| 4 | 0.0 |
| 5 | 0.0 |
| 6 | 0.0 |
| GFP | 0.0 |

| ZFN Pair B | |
|---|---|
| group | %NHEJ |
| 1 | 78.6 |
| 2 | 24.0 |
| 3 | 15.6 |
| 4 | 8.6 |
| 5 | 7.5 |
| 6 | 59.5 |
| GFP | 0.0 |

| ZFN Pair C | |
|---|---|
| group | %NHEJ |
| 1 | 2.5 |
| 2 | 5.6 |
| 3 | 2.0 |
| 4 | 1.9 |
| 5 | 2.1 |
| 6 | 3.6 |
| GFP | 0.0 |

| ZFN Pair D | |
|---|---|
| group | %NHEJ |
| 1 | 13.1 |
| 2 | 20.8 |
| 3 | 0.0 |
| 4 | 0.0 |
| 5 | 0.0 |
| 6 | nd |
| GFP | 0.0 |

9 bp gap

| ZFN Pair E | |
|---|---|
| group | %NHEJ |
| 1 | 6.2 |
| 2 | 4.9 |
| 3 | 0.0 |
| 4 | nd |
| 5 | 0.0 |
| 6 | 0.0 |
| GFP | 0.0 |

| ZFN Pair F | |
|---|---|
| group | %NHEJ |
| 1 | 16.6 |
| 2 | 33.6 |
| 3 | 0.0 |
| 4 | 0.0 |
| 5 | 0.0 |
| 6 | 11.1 |
| GFP | 0.0 |

| ZFN Pair G | |
|---|---|
| group | %NHEJ |
| 1 | 26.9 |
| 2 | 37.6 |
| 3 | 2.2 |
| 4 | 0.0 |
| 5 | 0.0 |
| 6 | 12.4 |
| GFP | 0.0 |

| ZFN Pair H | |
|---|---|
| group | %NHEJ |
| 1 | 39.8 |
| 2 | 72.6 |
| 3 | 24.8 |
| 4 | 15.0 |
| 5 | 7.7 |
| 6 | 63.3 |
| GFP | 0.0 |

```
Group 1: L8c  [ZFP]HAQRC-NGSYAPMPPLALASPELEEKKSEL[wt FokI]
Group 2: L8c  [ZFP]HAQRC-NGSYAPMPPLALASPELEEKKSEL[eHiFi FokI]
Group 3: L8n  [ZFP]HTKIH-NGSYAPMPPLALASPELEEKKSEL[eHiFi FokI]
Group 4: L8o  [ZFP]HTKIH-GGSYAPMPPLALASPELEEKKSEL[eHiFi FokI]
Group 5: L8m  [ZFP]HTKIH--GSYAPMPPLALASPELEEKKSEL[eHiFi FokI]
Group 6: L8p  [ZFP]HTKIHLRGSYAPMPPLALASPELEEKKSEL[eHiFi FokI]
```

Figure 13

| Name | Linker Sequence | NHEJ% ZFN pair #1 | ZFN pair #1 |
|---|---|---|---|
| L7a | HTKIH LRGSQLVKSKSEAAAR ELEEK | 12.6% | 11.9% |
| L7c4 | HTKIH LRGSPISRARPLNPHP ELEEK | 8.1% | 18.7% |
| L7c5 | HTKIH LRGSISRARPLNPHP ELEEK | 19.8% | 18.0% ↓ |
| L7c6 | HTKIH LRGSPSRARPLNPHP ELEEK | 17.3% | 14.5% |
| L7c7 | HTKIH LRGSSRARPLNPHP ELEEK | 12.9% | 13.4% |
| L7e4 | HTKIH LRGSYAPMPPLALASP ELEEK | 19.6% | 18.2% ↓ |
| L7e5 | HTKIH LRGSAPMPPLALASP ELEEK | 14.4% | 15.0% |
| L7e6 | HTKIH LRGSPMPPLALASP ELEEK | 15.8% | 13.2% |
| L7e7 | HTKIH LRGSMPPLALASP ELEEK | 5.3% | 8.8% |

Figure 15

| Variants | aa | Junction | Left ZFN Variants | Right ZFN variants | Left and right ZFN variants |
|---|---|---|---|---|---|
| V1 | -3 | HTKIHLRGS-------KSELEEK | 47.1 | 56.3 | 68.7 |
| V2 | -2 | HTKIHLRGS------GKSELEEK | 61.3 | 58.5 | 40.6 |
| V3 | -2 | HTKIHLRGS------VKSELEEK | 50.1 | 59.0 | 41.2 |
| V4 | -2 | HTKIHLRGS------EKSELEEK | 38.2 | 39.5 | 52.3 |
| V5 | -1 | HTKIHLRGS-----GVKSELEEK | 23.6 | 39.0 | 32.6 |
| V6 | -1 | HTKIHLRGS-----SVKSELEEK | 32.2 | 50.8 | 45.8 |
| V7 | -1 | HTKIHLRGS-----LVKSELEEK | 35.5 | 63.5 | 50.1 |
| V8 | -1 | HTKIHLRGS-----EVKSELEEK | 24.3 | 64.3 | 45.3 |
| V9 | 0 | HTKIHLRGS----GLVKSELEEK | 44.6 | 28.8 | 30.1 |
| V10 | 0 | HTKIHLRGS----SLVKSELEEK | 44.6 | 56.8 | 16.6 |
| V11 | 0 | HTKIHLRGS----RLVKSELEEK | 24.7 | 47.0 | 41.1 |
| V12 | 0 | HTKIHLRGS----WLVKSELEEK | 16.2 | 22.3 | 36.5 |
| V13 | 0 | HTKIHLRGS----QGVKSELEEK | 41.3 | 62.5 | 42.1 |
| V14 | 0 | HTKIHLRGS----QSVKSELEEK | 27.1 | 56.2 | 31.8 |
| V15 | 0 | HTKIHLRGS----QLSKSELEEK | 40.6 | 47.5 | 57.1 |
| V16 | +1 | HTKIHLRGS---GQLVKSELEEK | 20.3 | 42.4 | 51.0 |
| V17 | +1 | HTKIHLRGS---SQLVKSELEEK | 62.7 | 36.7 | 33.5 |
| V18 | +1 | HTKIHLRGS---KQLVKSELEEK | 50.1 | 57.7 | 22.5 |
| V19 | +1 | HTKIHLRGS---RQLVKSELEEK | 27.0 | 57.9 | 32.2 |
| V20 | +2 | HTKIHLRGS--GSQLVKSELEEK | 26.8 | 38.8 | 41.6 |
| V21 | +2 | HTKIHLRGS--GKQLVKSELEEK | 50.5 | 49.4 | 30.6 |
| V22 | +2 | HTKIHLRGS--TKQLVKSELEEK | 46.1 | 49.8 | 41.1 |
| V23 | +3 | HTKIHLRGSGTKQLVKSELEEK | 53.8 | 41.4 | 16.2 |
| V24 | +3 | HTKIHLRGSVTKQLVKSELEEK | 66.0 | 52.2 | 41.1 |
| Conventional | 0 | HTKIHLRGS----QLVKSELEEK | 45.4 | | |
| EGFP | | | 0.1 | | |

Figure 16

Pair 1 variants

| LEFT\RIGHT | GS-------KS | GS-----VKS | GS----EVKS | GS---QSVKS | GS--KQLVKS | GS-TKQLVKS | GSVTKQLVKS | GS----QLVKS | Average |
|---|---|---|---|---|---|---|---|---|---|
| GS-------KS | 0.7 | 3.8 | 4.6 | 3.3 | 5.7 | 3.7 | | 7.1 | 4.2 |
| GS-----VKS | 7.1 | 19.5 | 21.7 | 16.6 | 21.3 | 18.9 | | 21.5 | 18.0 |
| GS----EVKS | 17.3 | 26.5 | 24.8 | 22.5 | 27.1 | 24.4 | | 22.3 | 23.5 |
| GS---QSVKS | 16.6 | 23.9 | 24.1 | 24.2 | 25.3 | 25.7 | | 23.5 | 23.3 |
| GS--KQLVKS | 16.0 | 23.3 | 29.2 | 28.6 | 27.1 | 32.3 | | 27.3 | 26.1 |
| GS-GKQLVKS | 15.1 | 22.4 | 28.8 | 27.2 | 29.3 | 31.7 | | 25.8 | 25.8 |
| GSVTKQLVKS | 18.1 | 26.7 | 32.4 | 31.7 | 33.4 | 36.0 | | 27.0 | 29.4 |
| GS----QLVKS | 18.1 | 28.0 | 31.5 | 28.6 | 25.0 | 30.0 | | 17.2 | 25.9 |
| Average | 13.6 | 21.8 | 24.7 | 22.8 | 24.3 | 25.3 | | 21.5 | |

Pair 2 variants

| LEFT\RIGHT | GS-------KS | GS-----VKS | GS----EVKS | GS---QSVKS | GS--KQLVKS | GS-TKQLVKS | GSVTKQLVKS | GS----QLVKS | Average |
|---|---|---|---|---|---|---|---|---|---|
| GS-------KS | 0.4 | 1.9 | 1.7 | 0.9 | 1.7 | 1.6 | | 1.5 | 1.4 |
| GS-----VKS | 3.5 | 10.9 | 7.7 | 4.1 | 4.9 | 6.1 | | 7.1 | 6.6 |
| GS----EVKS | 9.6 | 16.6 | 13.8 | 12.3 | 12.1 | 11.7 | | 15.0 | 13.1 |
| GS---QSVKS | 10.1 | 16.4 | 14.2 | 13.7 | 14.0 | 12.4 | | 14.7 | 13.7 |
| GS--KQLVKS | 13.7 | 19.2 | 15.9 | 13.9 | 15.3 | 15.2 | | 16.4 | 15.8 |
| GS-GKQLVKS | 12.1 | 18.4 | 15.5 | 16.0 | 19.7 | 16.1 | | 15.9 | 16.5 |
| GSVTKQLVKS | 15.1 | 20.6 | 15.5 | 18.7 | 19.9 | 18.0 | | 19.3 | 18.3 |
| GS----QLVKS | 8.3 | 7.9 | 5.5 | 8.7 | 6.7 | 7.1 | | 11.1 | 7.9 |
| Average | 9.1 | 14.0 | 11.2 | 11.1 | 11.8 | 11.0 | | 12.6 | |

SEQUENCE LISTING

```
<160> NUMBER OF SEQ ID NOS: 312

<210> SEQ ID NO 1
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30
```

```
Gly Ile His Gly Val Pro Ala Met Ala Glu Arg Pro Phe Gln Cys
             35                  40                  45

Arg Ile Cys Met Arg Asn Phe Ser Asp Arg Ser Asn Leu Ser Arg His
 50                  55                  60

Ile Arg Thr His Thr Gly Glu Lys Pro Phe Ala Cys Asp Ile Cys Gly
 65                  70                  75                  80

Arg Lys Phe Ala Ile Ser Ser Asn Leu Asn Ser His Thr Lys Ile His
                 85                  90                  95

Thr Gly Ser Gln Lys Pro Phe Gln Cys Arg Ile Cys Met Arg Asn Phe
                100                 105                 110

Ser Arg Ser Asp Asn Leu Ala Arg His Ile Arg Thr His Thr Gly Glu
            115                 120                 125

Lys Pro Phe Ala Cys Asp Ile Cys Gly Arg Lys Phe Ala Thr Ser Gly
        130                 135                 140

Asn Leu Thr Arg His Thr Lys Ile His Leu Arg Gly Ser Gln Leu Val
145                 150                 155                 160

Lys Ser Glu Leu Glu Lys Lys Ser Glu Leu Arg His Lys Leu Lys
                165                 170                 175

Tyr Val Pro His Glu Tyr Ile Glu Leu Ile Glu Ile Ala Arg Asn Ser
                180                 185                 190

Thr Gln Asp Arg Ile Leu Glu Met Lys Val Met Glu Phe Phe Met Lys
                195                 200                 205

Val Tyr Gly Tyr Arg Gly Lys His Leu Gly Gly Ser Arg Lys Pro Asp
            210                 215                 220

Gly Ala Ile Tyr Thr Val Gly Ser Pro Ile Asp Tyr Gly Val Ile Val
225                 230                 235                 240

Asp Thr Lys Ala Tyr Ser Gly Gly Tyr Asn Leu Pro Ile Gly Gln Ala
                245                 250                 255

Asp Glu Met Gln Arg Tyr Val Glu Glu Asn Gln Thr Arg Asn Lys His
            260                 265                 270

Ile Asn Pro Asn Glu Trp Trp Lys Val Tyr Pro Ser Ser Val Thr Glu
        275                 280                 285

Phe Lys Phe Leu Phe Val Ser Gly His Phe Lys Gly Asn Tyr Lys Ala
290                 295                 300

Gln Leu Thr Arg Leu Asn His Ile Thr Asn Cys Asn Gly Ala Val Leu
305                 310                 315                 320

Ser Val Glu Glu Leu Leu Ile Gly Gly Glu Met Ile Lys Ala Gly Thr
                325                 330                 335

Leu Thr Leu Glu Glu Val Arg Arg Lys Phe Asn Asn Gly Glu Ile Asn
            340                 345                 350

Phe

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 2

Asn Gly Ile Cys Pro Pro Pro Arg Pro Arg Thr Ser Pro Pro
 1               5                   10
```

```
<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 3

Thr Gly Thr Ala Pro Ile Glu Ile Pro Pro Glu Val Tyr Pro
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 4

Asn Gly Ser Tyr Ala Pro Met Pro Pro Leu Ala Leu Ala Ser Pro
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 5

Pro Gly Ile Tyr Thr Ala Pro Thr Ser Arg Pro Thr Val Pro Pro
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 6

Asn Gly Ser Gln Thr Pro Lys Arg Phe Gln Pro Thr His Pro Ser Ala
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: misc_feature
<222> LOCATION: (1)..(1)
<223> OTHER INFORMATION: May or may not be present

<400> SEQUENCE: 7

His Leu Pro Lys Pro Ala Asn Pro Phe Pro Leu Asp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 8

His Arg Asp Gly Pro Arg Asn Leu Pro Pro Thr Ser Pro Pro
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 9

His Arg Leu Pro Asp Ser Pro Thr Ala Leu Ala Pro Asp Thr Leu
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 10

Asp Pro Asn Ser Pro Ile Ser Arg Ala Arg Pro Leu Asn Pro His Pro
1               5                   10                  15

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 11

```
Tyr Gly Pro Arg Pro Thr Pro Arg Leu Arg Cys Pro Ile Asp Ser Leu
1               5                   10                  15

Ile Phe Arg

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 12

His Cys Pro Ala Ser Arg Pro Ile His Pro
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 13

Gly Leu Gln Ser Leu Ile Pro Gln Gln Leu Leu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 14

Gly Leu Gln Pro Thr Val Asn His Glu Tyr Asn Asn
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 15

Pro Ala Asn Ile His Ser Leu Ser Ser Pro Pro Leu
1               5                   10

<210> SEQ ID NO 16
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 16

Pro Ala Gly Leu Asn Thr Pro Cys Ser Pro Arg Ser Arg Ser Asn
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 17

Ala Thr Ile Thr Asp Pro Asn Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 18

Pro Pro His Lys Gly Leu Leu Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 19

Ser Val Ser Leu Pro Asp Thr His His
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: misc_feature
<222> LOCATION: (1)..(1)
<223> OTHER INFORMATION: May or may not be present

<400> SEQUENCE: 20

Gly Thr His Gly Ala Thr Pro Thr His Ser Pro
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 21

Val Ala Pro Gly Glu Ser Ser Met Thr Ser Leu
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 22

Leu Arg Gly Ser Pro Ile Ser Arg Ala Arg Pro Leu Asn Pro His Pro
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 23

Leu Arg Gly Ser Ile Ser Arg Ala Arg Pro Leu Asn Pro His Pro
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 24

Leu Arg Gly Ser Pro Ser Arg Ala Arg Pro Leu Asn Pro His Pro
```

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 25

Leu Arg Gly Ser Ser Arg Ala Arg Pro Leu Asn Pro His Pro
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 26

Leu Arg Gly Ser Tyr Ala Pro Met Pro Pro Leu Ala Leu Ala Ser Pro
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 27

Leu Arg Gly Ser Ala Pro Met Pro Pro Leu Ala Leu Ala Ser Pro
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 28

Leu Arg Gly Ser Pro Met Pro Pro Leu Ala Leu Ala Ser Pro
1               5                   10

<210> SEQ ID NO 29
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(4)
<223> OTHER INFORMATION: May or may not be present

<400> SEQUENCE: 29

Leu Arg Gly Ser Met Pro Pro Leu Ala Leu Ala Ser Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Leu Pro Lys Pro Ala Asn Pro Phe Pro Leu Asp
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Lys Pro Ala Asn
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Arg Pro Leu Asn
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Met Pro Pro Leu Ala
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

```
Pro Pro Pro Arg Pro
1               5

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Gly Ser
1

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Ser Glu Ala Ala Ala Arg
1               5

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Leu Glu Glu Lys Lys Ser Glu Leu Arg His Lys
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid that forms an alpha helix
<220> FEATURE:
<223> OTHER INFORMATION: See specification as filed for detailed
      description of substitutions and preferred embodiments

<400> SEQUENCE: 38

Glu Xaa Xaa Xaa Arg
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid that forms an alpha helix
```

```
<220> FEATURE:
<223> OTHER INFORMATION: See specification as filed for detailed
      description of substitutions and preferred embodiments

<400> SEQUENCE: 39

Glu Xaa Xaa Xaa Lys
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ala Ala Ala Arg
1               5

<210> SEQ ID NO 41
<211> LENGTH: 9
<212> TYPE: PRT
<213> ORGANISM: Unknown
<220> FEATURE:
<223> OTHER INFORMATION: Description of Unknown: "LAGLIDADG" family
      peptide motif sequence

<400> SEQUENCE: 41

Leu Ala Gly Leu Ile Asp Ala Asp Gly
1               5

<210> SEQ ID NO 42
<211> LENGTH: 25
<212> TYPE: DNA
<213> ORGANISM: Homo sapiens

<400> SEQUENCE: 42
ctgacctctt ctcttcctcc cacag                                          25

<210> SEQ ID NO 43
<211> LENGTH: 13
<212> TYPE: DNA
<213> ORGANISM: Homo sapiens

<400> SEQUENCE: 43
tttctctcca cag                                                       13

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Arg Gly Ser Gln Leu Val Lys Ser Glu Leu Glu Glu Lys Lys Ser
1               5                   10                  15

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 45

His Ala Gln Arg Cys Asn Gly Ser Tyr Ala Pro Met Pro Pro Leu Ala
1               5                   10                  15

Leu Ala Ser Pro Glu Leu Glu Glu Lys Lys Ser Glu Leu
            20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Thr Lys Ile His Asn Gly Ser Tyr Ala Pro Met Pro Pro Leu Ala
1               5                   10                  15

Leu Ala Ser Pro Glu Leu Glu Glu Lys Lys Ser Glu Leu
            20                  25

<210> SEQ ID NO 47
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Thr Lys Ile His Gly Gly Ser Tyr Ala Pro Met Pro Pro Leu Ala
1               5                   10                  15

Leu Ala Ser Pro Glu Leu Glu Glu Lys Lys Ser Glu Leu
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Thr Lys Ile His Gly Ser Tyr Ala Pro Met Pro Pro Leu Ala Leu
1               5                   10                  15

Ala Ser Pro Glu Leu Glu Glu Lys Lys Ser Glu Leu
            20                  25

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

His Thr Lys Ile His Leu Arg Gly Ser Tyr Ala Pro Met Pro Pro Leu
1               5                   10                  15

Ala Leu Ala Ser Pro Glu Leu Glu Glu Lys Lys Ser Glu Leu
            20                  25                  30

<210> SEQ ID NO 50

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Thr Lys Ile His Leu Arg Gly Ser
1               5

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Thr Lys Ile His Leu Arg Gly Ser Gln Leu Val Lys Ser Glu Leu
1               5                   10                  15

Glu Glu Lys

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Ala Glu Arg Pro Phe Gln Cys Arg Ile Cys Met Arg Asn Phe Ser
1               5                   10                  15

Arg Ser Asp Asn Leu Gly Val His Ile Arg Thr His Thr Gly Glu
            20                  25                  30

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Pro Phe Ala Cys Asp Ile Cys Gly Arg Lys Phe Ala Gln Lys Ile
1               5                   10                  15

Asn Leu Gln Val His Thr Lys Ile His Thr Gly Glu
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Pro Phe Gln Cys Arg Ile Cys Met Arg Asn Phe Ser Arg Ser Asp
1               5                   10                  15

Val Leu Ser Glu His Ile Arg Thr His Thr Gly Glu
            20                  25
```

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Pro Phe Ala Cys Asp Ile Cys Gly Arg Lys Phe Ala Gln Arg Asn
1               5                   10                  15

His Arg Thr Thr His Ala Gln Arg Cys Gly Leu Arg Gly Ser Gln Leu
            20                  25                  30

Val Lys Ser Glu Leu Glu Glu Lys
        35                  40

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 cctttttgcag tttatgataa actgcaaaag g                                31

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57 cctttttgcag tttatgcata aactgcaaaa gg                               32

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58 cctttttgcag tttatgacat aaactgcaaa agg                              33

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59 cctttttgcag tttatgagca taaactgcaa aagg                             34

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 60
ccttttgcag tttatgagta ccgatcataa actgcaaaag g                    41

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccttttgcag tttatgagta cgcgatcata aactgcaaaa gg                   42

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Arg Asn Pro Gly Thr Val Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

His Val Ala Arg Arg Lys Ser Asn
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Ser Thr Ile Pro Tyr Asn Phe
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Pro Pro Ala Asn Ser Pro Thr Pro
1               5

<210> SEQ ID NO 66
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 66

His Pro Leu Pro Pro Ile Arg Pro Val
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Val Ser His Arg Ser Thr Pro Ile
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Arg Pro Ile Arg His Pro Leu Pro
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Ala Ala Arg Leu His Pro Ala Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Ala Ser Pro Ala Leu Ser His Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Gly Lys Asp Gln Asn Arg Ile Pro
1               5
```

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Met Pro Phe Ala Arg Leu Arg Leu Thr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Ser Thr Leu Leu Val Tyr Arg Ala Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Tyr Ala Ser Thr Ser Cys Met Pro Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Thr Lys Thr Leu Pro Pro Pro Arg Pro
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Pro His Asn Arg Pro Arg Leu Thr Val Leu
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Arg Ala Arg Gln Arg Leu Arg Ser Ala Phe Pro
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Thr His Gly Ala Thr Pro Thr His Ser Pro
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Asp Ser Met Ile Thr Ala Ala Pro Phe Ile
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Arg Phe Gly Ile Arg Ser Tyr Pro His Glu Asp
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Leu Ser Ser Gln Pro Thr Leu Val Leu Cys Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Thr Leu Gly Pro Ser Cys Ala Ala Asp His Thr
1               5                   10

<210> SEQ ID NO 83
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Val Pro Asn Gln Pro Asp Arg Val His Thr Thr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Val Pro Pro His Met Ser His Asp Cys Asn Thr
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Ser Thr Tyr Ser Ser Thr Arg Pro Ile Ser Arg Pro
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Gln Gln Leu Phe Ala Lys Pro Thr His Pro Ile
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Pro Gly Gln Ser Arg Asn Val Phe Ser Thr Pro Pro
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Arg Ala Ile Ser Arg Asp Pro Val Asn Ile Arg Ile His
```

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Val Ala Thr His Pro Glu Gly Ala Ala Thr Pro Pro Arg
1               5                   10

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Ile Asn Leu His Ala Arg Asn Ser Val Ala Tyr His Pro Val
1               5                   10                  15

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

His Asp Met Pro Arg His Pro Phe
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Lys Gln Pro Gln Ala His Arg
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asn Leu Leu Pro Pro Ile Ala Gly Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

His Pro Arg Thr Arg Ser His Tyr Pro
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Arg Val Leu Ile Asn Pro Leu Val
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Ser Pro Ala Gln Ser Phe Pro His
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Arg Gln Thr Lys Asn Arg Ala Glu
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Thr Thr Pro Pro Arg Val Pro
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Asn Ser Cys Gly Asp Ser Pro Arg His
1               5                   10

<210> SEQ ID NO 100

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Leu Gly Pro Leu Pro Gln Ile Pro Pro
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Ser Ser Leu Arg Pro His Ala Tyr His
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

His Cys Pro Ala Ser Arg Pro Ile His Pro
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Pro Phe Leu Val Ala His Thr Pro Ile
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Pro Asn Gln Phe Arg Asp Asp Val Tyr
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105
```

```
Ser Leu His Thr Thr Ser Arg Arg Ser Ile
1               5                  10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Thr Tyr Tyr Pro Ser Pro Pro Leu Pro Thr
1               5                  10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Leu Ser Ala Thr Asn Pro Pro Phe Leu Asn
1               5                  10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Leu Gln Ser Leu Ile Pro Gln Gln Leu Leu
1               5                  10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Val Leu Pro Lys Pro Met Cys Asn Pro Pro Ser
1               5                  10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Pro Asp Leu Thr Asn Arg Ser His Ser Leu
1               5                  10

<210> SEQ ID NO 111
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 111

Ser Tyr Leu Ala Asn Leu Pro Tyr Pro His Leu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys His His Ala Pro Pro Ile Met Ser Arg Pro Ala
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Pro Ala His His Arg Pro Ala Gly Ile Pro Arg
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Pro Thr Pro Thr Leu His Asp Ala Tyr Ala Pro Ser
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Pro Thr Ala Tyr Pro Ser Arg Pro Thr Phe Thr Ser
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Pro Pro Ser Pro Pro Lys Asn Leu Asn His Arg Val
1               5                   10
```

```
<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Phe Arg Ser Ser His Asn Pro Val Pro Phe Thr Pro
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Ser Arg Ser Ser His Pro Val Leu Thr Ile Pro Ser
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Pro Ser Thr Gly Ala Asp His Thr Pro Leu Pro Ser Ala
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Gln Ile Asn Pro Pro Asp Asp Thr Ala Val Ser Lys Tyr
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Arg Pro Gln Pro Leu His Ser Arg Val His Leu His
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

```
His Arg Asp Gly Pro Arg Asn Leu Pro Pro Thr Ser Pro Pro
1               5                   10
```

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Pro Thr Arg His Pro Arg Ala Pro Ser Ser Ala Ala Phe His
1               5                   10
```

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Pro Thr Ala Gln Pro His Lys Ala His Pro Pro His Trp Pro
1               5                   10
```

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Arg Asn Thr Thr Pro Ile Pro Pro Ser Gly Gly Pro Glu Pro
1               5                   10
```

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Arg Gly Ile Gln His Lys Thr Gln Arg Thr His Pro Ser Pro
1               5                   10
```

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Leu Gly Ser Val Leu Pro Ser Pro Arg Trp Leu Pro Gly Pro
1               5                   10
```

<210> SEQ ID NO 128
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 128

Asp Pro Thr Ser Thr Arg Ser Ser Asp Val Lys Phe Ser Pro
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Arg Asn Gly Ala Pro Arg Pro Arg Leu Asn Ile Leu Asn
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ser Val Lys His Arg Pro Met Pro His Arg His Pro Ala
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Val Arg Arg Thr Ser Arg Leu Asp Leu Asn Ala Gln Ser
1               5                   10

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asn Gly Met Ala Met Thr Gln Tyr Arg Pro Leu Asp His Asn Pro
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Gly Trp Asn His Ala Phe Arg Pro Ala Val Pro Ser Ala Pro
1               5                   10                  15
```

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Arg Gly Leu Ser Thr Pro Arg Asp Val Pro Thr Val Leu Pro
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Ser Pro Asp Phe His Pro Pro Thr Thr Asn Leu Ser Leu Pro
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Pro Arg Pro Gln Thr Gly Glu Gln Ile Thr Gln Pro Ser Leu
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Pro Gly Pro His Thr Gln Ser Gln Thr Leu Arg Thr Pro Ser His
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Arg Ala Gly Thr Thr Pro Pro Ile Asn Thr Leu Pro Thr Arg
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 139

Ala Leu Tyr Thr Gln Gly Pro Val Arg Pro Ala Arg Thr Pro Pro
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Arg Gly Leu Gly Leu Thr Leu His Arg Val Pro Asn His Pro
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Leu Leu Tyr Ser Ile Pro Asn Leu Ala Arg Val Ser His Ser
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Phe Pro Gln Pro His Arg Arg Arg Ala Ala Leu Val Cys Pro
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Gly Ser Asn Pro Thr Pro Ser Arg Val Leu Thr Pro Ile Thr
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Gly His Thr Gly His Arg Asp Lys Pro Ala Ala Leu Val Thr Arg
1               5                   10                  15

<210> SEQ ID NO 145
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 145

Thr Gly Ile Phe Arg Ile Leu Asp Val Ser Pro Ala Asn Gly Ser Pro
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Leu Asn Ala His Ala Pro Lys Ser Arg Arg Thr Leu Glu Pro Pro
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Leu Arg Pro Asn Ser Leu Ser Ala Leu Arg Ser Ser Ser Pro Leu Ile
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Pro Asn Ser Pro Ile Ser Arg Ala Arg Pro Leu Asn Pro His Pro
1               5                   10                  15

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Gly Gln Ala Val Tyr Asp Thr Pro Pro Thr Pro
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Gly Ile Cys Pro Pro Pro Arg Pro Arg Thr Ser Pro Pro
1               5                   10
```

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Lys Gly Val His Lys Ala Thr Pro Pro Ala Ser Pro Ser Tyr
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Gly Thr Arg Ser Pro Val Ser Thr Pro Ile Ser His Pro
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Thr Gly Ser Val His Pro Ser Arg Pro Pro Leu His Asn Ser
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Ile Ile Ser Pro Pro Leu Pro Pro Ser Ala Pro Leu Pro
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Pro Gly Val Ala Pro Leu Arg Pro Lys Asn Arg Val His Pro
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 156

Pro Val Thr Thr Tyr Thr Arg Met Ala His Pro Thr Thr Pro
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Leu Gly Leu Asn Ala Pro Val Lys Thr Pro Pro Leu Pro
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Leu Gly Leu Asn Ala Pro Val Thr Thr Pro Pro Leu Pro
1               5                   10

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Ala Ser Ala Pro Ala Met Arg Pro Val Val Val Gln Asn Ala
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Gly Lys Asn Ser Thr Ser Phe Thr Thr Arg Gly Thr Ile Pro
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Gly Thr Val His Thr Ser Pro Ile Cys Pro Gln Thr Tyr Pro
1               5                   10                  15

<210> SEQ ID NO 162
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Gly Val Leu Arg Arg Ser Phe His Arg Pro Pro Ile Val Leu
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Pro His Ile Thr Thr Arg His Ser Gln Pro Lys Thr His Pro Val
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Pro Gln Phe Arg Ala Pro Ala Lys Pro Pro Leu His Asn Thr Arg
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Gly Glu Arg His Arg Val Arg Pro Thr Ala Pro Pro Thr Leu
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Ala Pro Val Ala Ser Arg Leu Leu Pro Pro Lys Ser Leu Pro
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Ser Ile Pro Pro Arg Arg Thr Gln Val Arg Thr Pro Thr Pro
```

```
<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asn Gly Ser Gln Thr Pro Lys Arg Phe Gln Pro Thr His Pro Ser Ala
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Pro Thr Arg Pro Ser Pro Ser Gly Leu Asn Thr Pro Val Pro Asn Pro
1               5                   10                  15

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Lys Leu Asp Thr Pro Thr Ala His Thr Pro Val Ser Arg Thr Ser
1               5                   10                  15
Pro

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Asn Leu Arg Pro Ser Pro His Val Asn Ser Ser Pro Pro His Ser
1               5                   10                  15
Ser

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Asn Lys Arg Thr Asn Leu Ser
1               5

<210> SEQ ID NO 173
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Pro Ala Pro Ile Pro Thr Ser
1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Thr Pro Asn Ala Lys Leu Pro His
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

His Pro Ile His Pro Gly Ile Tyr
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

His Pro Arg Lys Pro Val Pro Phe
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

His Gly Pro Arg His Thr Pro Val
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Val Ala Ala Ala Ser Pro Pro
```

```
<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asn Ile Arg Asn Tyr Asn Ala Ala Ala
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Pro Pro Pro His Ser Pro Pro Pro Phe
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Pro Phe Pro Tyr Ser Ser Pro His His
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu Pro Ala Arg Pro Gly Ile Pro His
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Leu Cys Cys His Ser Arg Pro Ala Asn
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                    peptide

<400> SEQUENCE: 184

Leu Pro Asn Met Thr Leu Lys Pro Tyr
1               5

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Thr Asp Ser Arg His Arg Arg Ser Ile Ile
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Pro Ser His Phe Arg Pro Val Pro Pro
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Phe Thr Pro Gly His His His Pro His Thr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Phe Ser Thr Pro Asn Thr Pro Arg Ile Asn
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Val Thr Gly Ser His Thr Arg Asp Thr Ile
1               5                   10

<210> SEQ ID NO 190
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Leu Phe Pro Leu Arg Pro His Leu Pro Pro
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Lys Ser Pro Glu Ala Pro Asn Pro Ile Ala Phe Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Pro Leu Leu Arg Thr His Val Gly Phe Pro Arg
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Ser Leu Val Met Ala Asp Pro His Tyr Gln Phe
1               5                   10

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Pro Leu Ala Asn Ser Thr Ser Ala His Pro Ala Arg Met Pro Glu
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195
```

```
Ala Pro Ala Cys His Thr Thr Pro Asn Ala Pro Arg Tyr Pro Leu
 1               5                  10                  15
```

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Gly Asn Thr Leu Thr Ile Arg Ser Glu Gln Asp Leu Val Val Ile
 1               5                  10                  15
```

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Tyr His Thr Pro Leu Asn Tyr Pro Leu Leu Pro Asp His Tyr Tyr
 1               5                  10                  15
```

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
His Ser Pro Arg Arg Ser Asp Pro Pro Ala Pro His Ser Asp Glu Ala
 1               5                  10                  15
```

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

```
His Pro Pro Gln His Phe Gly His
 1               5
```

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

```
His Ser Lys Thr Thr Asn Leu Thr Pro
 1               5
```

<210> SEQ ID NO 201
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 201

Gly Ala Thr Pro Thr Lys Leu Leu Pro
1               5

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asn Arg Arg Ser Ser Pro Arg Pro Arg Thr
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

His Ser Asn Phe Gln Asp Ile Lys Glu Ile
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Leu Phe Pro Gln Pro Glu Leu Pro Cys
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Arg Pro Lys Tyr Pro Thr Pro His Leu Asp
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Thr Asn Lys Tyr Pro Phe Val Ala His Leu
1               5                   10

```
<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Ser Ser His Asp Thr Arg Arg Pro His Val
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Ala Arg Leu Pro Ala Gly His Asn His Thr
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Leu Leu Pro Leu Ala Pro Lys Tyr His Phe
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Ile Pro Asp Leu Pro Val Phe Ser Thr Ile Pro
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Leu Pro Pro Thr Pro Ser Phe Pro Pro Pro Trp
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212
```

```
Pro Ser Leu Asp Thr Pro Ala Ile Ile Pro Thr Val His
1               5                   10
```

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

```
Pro His Arg Gly Ala Ser Ser Thr Gln Cys Leu Ser His
1               5                   10
```

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Pro Ser Arg Ser Pro Ala Ser Thr Leu Ser Pro Arg His
1               5                   10
```

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Pro Val Ala His Pro Arg Pro Asp Leu His Pro Thr Thr Thr
1               5                   10
```

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Ala Ala Arg His Gln Asn Asp Leu Thr Ser Pro Ala Tyr Ser
1               5                   10
```

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Gly Thr Asn Pro Pro Asn Thr Asn Pro Arg His Ser His Tyr
1               5                   10
```

<210> SEQ ID NO 218
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 218

Gly Pro Ala Lys Ser Pro Pro Asn Pro Ser Ser Thr Arg Val
1               5                   10

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Asn Ser Ile Leu Asp Pro Arg Ser Ala Thr Arg Ala His Leu
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Pro Lys Pro Pro Pro Leu Phe Ser Ser Pro Arg Ile Asn Asn Pro
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Val Gly Thr His Pro Ala Ser Ser Val Arg Ser Asp Trp Pro
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Asn Ser Asp Pro Leu Ala Ser Ala Pro Arg Arg Glu Pro Arg Leu
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ser Ser Asn Arg Pro Asn Pro His Ala Thr Lys Trp Met Pro Thr His
1               5                   10                  15
```

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Gln Pro Lys Ala Thr Thr Ser Ala Arg Arg Pro Asn Thr Thr Thr
1               5                   10                  15

<210> SEQ ID NO 225
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Thr Arg Ser Thr Ser His Lys Ala Arg Asp Asp Thr Arg Pro Ile Pro
1               5                   10                  15

Cys

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg His Ala Ala Asn Pro Pro Ser Arg His Cys Arg Thr Ala Pro His
1               5                   10                  15

Pro

<210> SEQ ID NO 227
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gtcatcctca tccgtttaaa ctgcaaaag                                    29

<210> SEQ ID NO 228
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtcatcctca tcctgtttaa actgcaaaag                                   30

<210> SEQ ID NO 229
<211> LENGTH: 31
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 229
gtcatcctca tcctggttta aactgcaaaa g                                   31

<210> SEQ ID NO 230
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gtcatcctca tcctgagttt aaactgcaaa ag                                  32

<210> SEQ ID NO 231
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gtcatcctca tcctgatact gctgtttaaa ctgcaaaag                           39

<210> SEQ ID NO 232
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gtcatcctca tcctgatact agctgtttaa actgcaaaag                          40

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Leu Arg Gly Ser Gln Leu Val Lys Ser Lys Ser Glu Ala Ala Ala
1               5                   10                  15

Arg

<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Gly Leu Met Pro Pro Ser His Pro Arg Gln Pro Ile His Ile Asn
1               5                   10                  15

Phe

<210> SEQ ID NO 235

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Thr Gly Ser Gly Thr Pro Thr Arg Pro His Pro Pro Leu Pro Pro
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Arg Pro Arg Arg Pro Thr Asp Thr Pro Leu Gly Ser Pro Pro
1               5                   10                  15

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

His Thr Thr Pro Asn Pro His Ala Asn Thr
1               5                   10

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile Leu Thr Pro Val Thr His Val Val
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

His Arg Ile Leu Ser Pro Ser Arg Gly
1               5

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240
```

```
Gly Thr Pro Arg Ala Ser Ser Asp Ser Ser Phe
1               5                   10
```

<210> SEQ ID NO 241
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)
<220> FEATURE:
<221> NAME/KEY: CDS
<222> LOCATION: (55)..(75)

<400> SEQUENCE: 241

```
atc cac ggg gta ccg agaccggcat taagcttgat atctcaggcc acggtctcc      54
Ile His Gly Val Pro
1               5 gag ctg gag gag aag aag tcc                                          75
Glu Leu Glu Glu Lys Lys Ser
                10
```

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Ile His Gly Val Pro Glu Leu Glu Glu Lys Lys Ser
1               5                   10
```

<210> SEQ ID NO 243
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(48)

<400> SEQUENCE: 243

```
aga tgc aac ggt atc tgc cca cct cca agg ccc agg acc tcc cca cca     48
Arg Cys Asn Gly Ile Cys Pro Pro Pro Arg Pro Arg Thr Ser Pro Pro
1               5                   10                  15
```

<210> SEQ ID NO 244
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Arg Cys Asn Gly Ile Cys Pro Pro Pro Arg Pro Arg Thr Ser Pro Pro
1               5                   10                  15
```

<210> SEQ ID NO 245
<211> LENGTH: 51
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 245 aga tgc aac ggt tcc tac gct cca atg cca ccc ctg gct ctg gct tcc    48
Arg Cys Asn Gly Ser Tyr Ala Pro Met Pro Pro Leu Ala Leu Ala Ser
1               5                   10                  15 cca                                                                51
Pro

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Cys Asn Gly Ser Tyr Ala Pro Met Pro Pro Leu Ala Leu Ala Ser
1               5                   10                  15

Pro

<210> SEQ ID NO 247
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 247 aga tgc cca ggt atc tac acc gct cca acc tcc agg cca acc gtg cct    48
Arg Cys Pro Gly Ile Tyr Thr Ala Pro Thr Ser Arg Pro Thr Val Pro
1               5                   10                  15 cca                                                                51
Pro

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Arg Cys Pro Gly Ile Tyr Thr Ala Pro Thr Ser Arg Pro Thr Val Pro
1               5                   10                  15

Pro

<210> SEQ ID NO 249
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
```

```
<222> LOCATION: (1)..(57)

<400> SEQUENCE: 249 aga tgc acc ggc ctg atg cca ccc tcc cac cca agg cag cca atc cac      48
Arg Cys Thr Gly Leu Met Pro Pro Ser His Pro Arg Gln Pro Ile His
1               5                   10                  15 atc aac ttc                                                          57
Ile Asn Phe <210> SEQ ID NO 250
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Arg Cys Thr Gly Leu Met Pro Pro Ser His Pro Arg Gln Pro Ile His
1               5                   10                  15

Ile Asn Phe

<210> SEQ ID NO 251
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 251 cat acc aag ata cac ctg cgc caa aaa gat gcg gcc cgg gga tcc          45
His Thr Lys Ile His Leu Arg Gln Lys Asp Ala Ala Arg Gly Ser
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

His Thr Lys Ile His Leu Arg Gln Lys Asp Ala Ala Arg Gly Ser
1               5                   10                  15

<210> SEQ ID NO 253
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 253 cat acc aag ata tgc cgagacgaaa aagatgcggc ccgg                       39
His Thr Lys Ile Cys
1               5

<210> SEQ ID NO 254
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

His Thr Lys Ile Cys
1               5

<210> SEQ ID NO 255
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 255 cat gcc cag aga tgc cgagaccaaa aagatgcggc ccgg                         39
His Ala Gln Arg Cys
1               5

<210> SEQ ID NO 256
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

His Ala Gln Arg Cys
1               5

<210> SEQ ID NO 257
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(15)

<400> SEQUENCE: 257 cat gcc cag aga tgc                                                    15
His Ala Gln Arg Cys
1               5

<210> SEQ ID NO 258
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

His Ala Gln Arg Cys His Leu Pro Lys Pro Ala Asn Pro Phe Pro Leu
1               5                   10                  15

Asp Glu Leu Glu Glu Lys
            20
```

<210> SEQ ID NO 259
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

His Ala Gln Arg Cys Asp Pro Asn Ser Pro Ile Ser Arg Ala Arg Pro
1               5                   10                  15

Leu Asn Pro His Pro Glu Leu Glu Glu Lys
            20                  25

<210> SEQ ID NO 260
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

His Ala Gln Arg Cys Asn Gly Ile Cys Pro Pro Pro Arg Pro Arg Thr
1               5                   10                  15

Ser Pro Pro Glu Leu Glu Glu Lys
            20

<210> SEQ ID NO 261
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

His Ala Gln Arg Cys Asn Gly Ser Tyr Ala Pro Met Pro Pro Leu Ala
1               5                   10                  15

Leu Ala Ser Pro Glu Leu Glu Glu Lys
            20                  25

<210> SEQ ID NO 262
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

His Thr Lys Ile His His Leu Pro Lys Pro Ala Asn Pro Phe Pro Leu
1               5                   10                  15

Asp Glu Leu Glu Glu Lys
            20

<210> SEQ ID NO 263
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Thr Lys Ile His Asp Pro Asn Ser Pro Ile Ser Arg Ala Arg Pro
1               5                   10                  15

Leu Asn Pro His Pro Glu Leu Glu Glu Lys
            20                  25

<210> SEQ ID NO 264
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

His Thr Lys Ile His Asn Gly Ile Cys Pro Pro Arg Pro Arg Thr
1               5                   10                  15

Ser Pro Pro Glu Leu Glu Glu Lys
            20

<210> SEQ ID NO 265
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

His Thr Lys Ile His Asn Gly Ser Tyr Ala Pro Met Pro Pro Leu Ala
1               5                   10                  15

Leu Ala Ser Pro Glu Leu Glu Glu Lys
            20                  25

<210> SEQ ID NO 266
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

His Thr Lys Ile His Leu Pro Lys Pro Ala Asn Pro Phe Pro Leu Asp
1               5                   10                  15

Glu Leu Glu Glu Lys
            20

<210> SEQ ID NO 267
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

His Thr Lys Ile His Pro Asn Ser Pro Ile Ser Arg Ala Arg Pro Leu
1               5                   10                  15

Asn Pro His Pro Glu Leu Glu Glu Lys
            20                  25

<210> SEQ ID NO 268
<211> LENGTH: 23
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 268

His Thr Lys Ile His Gly Ile Cys Pro Pro Arg Pro Arg Thr Ser
1               5                   10                  15

Pro Pro Glu Leu Glu Glu Lys
            20

<210> SEQ ID NO 269
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

His Thr Lys Ile His Gly Ser Tyr Ala Pro Met Pro Pro Leu Ala Leu
1               5                   10                  15

Ala Ser Pro Glu Leu Glu Glu Lys
            20

<210> SEQ ID NO 270
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

His Thr Lys Ile His Leu Arg Gly Ser Gln Leu Val Lys Ser Lys Ser
1               5                   10                  15

Glu Ala Ala Ala Arg Glu Leu Glu Glu Lys
            20                  25

<210> SEQ ID NO 271
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

His Thr Lys Ile His Leu Arg Gly Ser Gln Leu Val Lys Ser Lys Ser
1               5                   10                  15

Glu Ala Ala Ala Arg Glu Leu Glu Glu Lys
            20                  25

<210> SEQ ID NO 272
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

His Thr Lys Ile His Leu Arg Gly Ser Pro Ile Ser Arg Ala Arg Pro
1               5                   10                  15

Leu Asn Pro His Pro Glu Leu Glu Glu Lys
            20                  25
```

<210> SEQ ID NO 273
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

His Thr Lys Ile His Leu Arg Gly Ser Ile Ser Arg Ala Arg Pro Leu
1               5                   10                  15

Asn Pro His Pro Glu Leu Glu Glu Lys
            20                  25

<210> SEQ ID NO 274
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

His Thr Lys Ile His Leu Arg Gly Ser Pro Ser Arg Ala Arg Pro Leu
1               5                   10                  15

Asn Pro His Pro Glu Leu Glu Glu Lys
            20                  25

<210> SEQ ID NO 275
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

His Thr Lys Ile His Leu Arg Gly Ser Ser Arg Ala Arg Pro Leu Asn
1               5                   10                  15

Pro His Pro Glu Leu Glu Glu Lys
            20

<210> SEQ ID NO 276
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

His Thr Lys Ile His Leu Arg Gly Ser Tyr Ala Pro Met Pro Pro Leu
1               5                   10                  15

Ala Leu Ala Ser Pro Glu Leu Glu Glu Lys
            20                  25

<210> SEQ ID NO 277
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

-continued

```
His Thr Lys Ile His Leu Arg Gly Ser Ala Pro Met Pro Pro Leu Ala
1               5                   10                  15

Leu Ala Ser Pro Glu Leu Glu Glu Lys
            20                  25

<210> SEQ ID NO 278
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

His Thr Lys Ile His Leu Arg Gly Ser Pro Met Pro Pro Leu Ala Leu
1               5                   10                  15

Ala Ser Pro Glu Leu Glu Glu Lys
            20

<210> SEQ ID NO 279
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

His Thr Lys Ile His Leu Arg Gly Ser Met Pro Pro Leu Ala Leu Ala
1               5                   10                  15

Ser Pro Glu Leu Glu Glu Lys
            20

<210> SEQ ID NO 280
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

His Thr Lys Ile His Leu Arg Gly Ser Lys Ser Glu Leu Glu Glu Lys
1               5                   10                  15

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

His Thr Lys Ile His Leu Arg Gly Ser Gly Lys Ser Glu Leu Glu Glu
1               5                   10                  15

Lys

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 282

His Thr Lys Ile His Leu Arg Gly Ser Val Lys Ser Glu Leu Glu Glu
1               5                   10                  15

Lys

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

His Thr Lys Ile His Leu Arg Gly Ser Glu Lys Ser Glu Leu Glu Glu
1               5                   10                  15

Lys

<210> SEQ ID NO 284
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

His Thr Lys Ile His Leu Arg Gly Ser Gly Val Lys Ser Glu Leu Glu
1               5                   10                  15

Glu Lys

<210> SEQ ID NO 285
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

His Thr Lys Ile His Leu Arg Gly Ser Ser Val Lys Ser Glu Leu Glu
1               5                   10                  15

Glu Lys

<210> SEQ ID NO 286
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

His Thr Lys Ile His Leu Arg Gly Ser Leu Val Lys Ser Glu Leu Glu
1               5                   10                  15

Glu Lys

<210> SEQ ID NO 287
<211> LENGTH: 18
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 287

His Thr Lys Ile His Leu Arg Gly Ser Glu Val Lys Ser Glu Leu Glu
1               5                   10                  15

Glu Lys

<210> SEQ ID NO 288
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

His Thr Lys Ile His Leu Arg Gly Ser Gly Leu Val Lys Ser Glu Leu
1               5                   10                  15

Glu Glu Lys

<210> SEQ ID NO 289
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

His Thr Lys Ile His Leu Arg Gly Ser Ser Leu Val Lys Ser Glu Leu
1               5                   10                  15

Glu Glu Lys

<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

His Thr Lys Ile His Leu Arg Gly Ser Arg Leu Val Lys Ser Glu Leu
1               5                   10                  15

Glu Glu Lys

<210> SEQ ID NO 291
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

His Thr Lys Ile His Leu Arg Gly Ser Trp Leu Val Lys Ser Glu Leu
1               5                   10                  15

Glu Glu Lys

<210> SEQ ID NO 292
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 292

His Thr Lys Ile His Leu Arg Gly Ser Gln Gly Val Lys Ser Glu Leu
1               5                   10                  15

Glu Glu Lys

<210> SEQ ID NO 293
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

His Thr Lys Ile His Leu Arg Gly Ser Gln Ser Val Lys Ser Glu Leu
1               5                   10                  15

Glu Glu Lys

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

His Thr Lys Ile His Leu Arg Gly Ser Gln Leu Ser Lys Ser Glu Leu
1               5                   10                  15

Glu Glu Lys

<210> SEQ ID NO 295
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

His Thr Lys Ile His Leu Arg Gly Ser Gly Gln Leu Val Lys Ser Glu
1               5                   10                  15

Leu Glu Glu Lys
            20

<210> SEQ ID NO 296
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

His Thr Lys Ile His Leu Arg Gly Ser Ser Gln Leu Val Lys Ser Glu
1               5                   10                  15

Leu Glu Glu Lys
            20

<210> SEQ ID NO 297
<211> LENGTH: 20
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

His Thr Lys Ile His Leu Arg Gly Ser Lys Gln Leu Val Lys Ser Glu
1               5                   10                  15

Leu Glu Glu Lys
            20

<210> SEQ ID NO 298
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

His Thr Lys Ile His Leu Arg Gly Ser Arg Gln Leu Val Lys Ser Glu
1               5                   10                  15

Leu Glu Glu Lys
            20

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

His Thr Lys Ile His Leu Arg Gly Ser Gly Ser Gln Leu Val Lys Ser
1               5                   10                  15

Glu Leu Glu Glu Lys
            20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

His Thr Lys Ile His Leu Arg Gly Ser Gly Lys Gln Leu Val Lys Ser
1               5                   10                  15

Glu Leu Glu Glu Lys
            20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

His Thr Lys Ile His Leu Arg Gly Ser Thr Lys Gln Leu Val Lys Ser
1               5                   10                  15

Glu Leu Glu Glu Lys
            20

<210> SEQ ID NO 302
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

His Thr Lys Ile His Leu Arg Gly Ser Gly Thr Lys Gln Leu Val Lys
1               5                   10                  15

Ser Glu Leu Glu Glu Lys
            20

<210> SEQ ID NO 303
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

His Thr Lys Ile His Leu Arg Gly Ser Val Thr Lys Gln Leu Val Lys
1               5                   10                  15

Ser Glu Leu Glu Glu Lys
            20

<210> SEQ ID NO 304
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Ser Lys Ser
1

<210> SEQ ID NO 305
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Ser Val Lys Ser
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gly Ser Glu Val Lys Ser
1               5

```
<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Ser Gln Ser Val Lys Ser
1               5

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Ser Lys Gln Leu Val Lys Ser
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Ser Gly Lys Gln Leu Val Lys Ser
1               5

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Ser Val Thr Lys Gln Leu Val Lys Ser
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Ser Gln Leu Val Lys Ser
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 312

Gly Ser Thr Lys Gln Leu Val Lys Ser
1               5
```

US 10,538,787 B2

COMPOSITIONS FOR LINKING DNA-BINDING DOMAINS AND CLEAVAGE DOMAINS

CROSS-REFERENCE TO RELATED APPLICATIONS

The present application is a continuation of U.S. patent application Ser. No. 14/471,782 filed Aug. 28, 2014 which claims the benefit of U.S. Provisional Application No. 61/871,219, filed Aug. 28, 2013, the disclosures of which are hereby incorporated by reference in their entireties.

STATEMENT OF RIGHTS TO INVENTIONS MADE UNDER FEDERALLY SPONSORED RESEARCH

Not applicable.

SEQUENCE LISTING

The instant application contains a Sequence Listing which has been submitted electronically in ASCII format and is hereby incorporated by reference in its entirety. Said ASCII copy, created on Jan. 5, 2017, is named 8325010801SL.txt and is 92,111 bytes in size.

TECHNICAL FIELD

The present disclosure is in the fields of genome and protein engineering.

BACKGROUND

Artificial nucleases, such as engineered zinc finger nucleases (ZFN), transcription-activator like effector nucleases (TALENs), the CRISPR/Cas system with an engineered crRNA/tracr RNA (single guide RNA') and/or nucleases based on the Argonaute system (e.g., from *T. thermophilus*, known as 'TtAgo', (Swarts et al (2014) *Nature* 507(7491): 258-261), comprising DNA binding domains (nucleotide or polypeptide) operably linked to cleavage domains have been used for targeted alteration of genomic sequences. For example, zinc finger nucleases have been used to insert exogenous sequences, inactivate one or more endogenous genes, create organisms (e.g., crops) and cell lines with altered gene expression patterns, and the like. See, e.g., U.S. Pat. Nos. 8,586,526; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130177960 and 20150056705, the disclosures of which are incorporated by reference in their entireties for all purposes. For instance, a pair of nucleases (e.g., zinc finger nucleases, TALENs) is typically used to cleave genomic sequences. Each member of the pair generally includes an engineered (non-naturally occurring) DNA-binding protein linked to one or more cleavage domains (or half-domains) of a nuclease. When the DNA-binding proteins bind to their target sites, the cleavage domains that are linked to those DNA binding proteins are positioned such that dimerization and subsequent cleavage of the genome can occur, generally between the pair of the zinc finger nucleases or TALENs.

It has been shown that cleavage activity of the nuclease pair is related to the length of the linker joining the zinc finger and the cleavage domain ("ZC" linker), the amino acid composition, and the distance between the target sites (binding sites). See, for example, U.S. Pat. Nos. 8,772,453; 7,888,121 and 8,409,861; Smith et al. (2000) *Nucleic Acids Res.* 28:3361-3369; Bibikova et al. (2001) *Mol. Cell. Biol.* 21:289-297. When using pairs of nuclease fusion proteins, optimal cleavage with currently available ZC linkers and cleavage half domains has been obtained when the binding sites for the fusion proteins are located 5 or 6 nucleotides apart (as measured from the near edge of each binding site). See, e.g., U.S. Pat. No. 7,888,121. U.S. Patent Publication 20090305419 describes linking DNA-binding domains and cleavage domains by using a ZC linker and modifying the N-terminal residues of the FokI cleavage domain.

Thus, there remains a need for methods and compositions that allow targeted modification where the artificial nucleases can cleave endogenous genomic sequences with binding site separations other than 5 bp or 6 bp. The ability to target sequences with different spacings would increase the number of genomic targets that can be cleaved. Altering the preferences between target sites separated by different numbers of base pairs could also allow the artificial nucleases to act with greater specificity.

SUMMARY

Disclosed herein are compositions for linking DNA-binding domains and cleavage domains to form nucleases, for example nucleases with altered target site separation (gap) preferences as compared to conventional linkers. Also described are fusion proteins comprising these linkers. The disclosure also provides methods of using these fusion proteins and compositions thereof for targeted cleavage of cellular chromatin in a region of interest and/or homologous recombination at a predetermined region of interest in cells.

Thus, in one aspect, described herein are amino acid sequences linking a DNA-binding domain (e.g., zinc finger protein or TAL-effector domain) to a cleavage domain (e.g., wild type or engineered FokI cleavage domain). In certain embodiments, the amino acid linker sequences extend between the last residue of the N- or C-terminal of the DNA-binding domain and the N- or C-terminal of the cleavage domain. In other embodiments, the linker may replace one or more residues of the DNA-binding domain and/or cleavage domain. In certain embodiments, the linker is 8, 9, 10, 11, 12, 13, 14, 15, 16, 17 or more residues in length. In other embodiments, the linker between the DNA-binding domain and the cleavage domain (or cleavage half-domain) comprises any of the linkers shown in FIGS. 4, 7, 9, 11, 12, 13, 15 and 16 (SEQ ID NOs: 2-21, 45-49, 51, 62-226, 233-240, and 258-312) (with or without 1 or more of the N-terminal amino acid residues shown in these Figures), including but not limited to (N)GICPPPRPRTSPP (SEQ ID NO:2); (T)GTAPIEIPPEVYP (SEQ ID NO:3); (N)GSYAPMPPLALASP (SEQ ID NO:4); (P)GIYTAPTSRPTVPP (SEQ ID NO:5); (N)GSQTP-KRFQPTHPSA (SEQ ID NO:6); (H)LPKPANPFPLD (SEQ ID NO:7); (H)RDGPRNLPPTSPP (SEQ ID NO:8); (H)RLPDSPTALAPDTL (SEQ ID NO:9); (DPNS)PIS-RARPLNPHP (SEQ ID NO:10); (Y)GPRPTPRLRCPID-SLIFR (SEQ ID NO:11); (H)CPASRPIHP (SEQ ID NO:12); (G)LQSLIPQQLL (SEQ ID NO:13); (G)LQPTVNHEYNN (SEQ ID NO:14); (P)ANIHSLSSPPPL (SEQ ID NO:15); (P)AGLNTPCSPRSRSN (SEQ ID NO:16); (A)TITDPNP (SEQ ID NO:17); (P)PHKGLLP (SEQ ID NO:18); (S)VS- LPDTHH (SEQ ID NO:19); (G)THGATPTHSP (SEQ ID NO:20); (V)APGESSMTSL (SEQ ID NO:21), (LRGS)PIS-RARPLNPHP (SEQ ID NO:22), (LRGS)ISRARPLNPHP (SEQ ID NO:23), (LRGS)PSRARPLNPHP (SEQ ID NO:24), (LRGS)SRARPLNPHP (SEQ ID NO:25), (LRGS) YAPMPPLALASP (SEQ ID NO:26), (LRGS)APMPPLA-LASP (SEQ ID NO:27), (LRGS)PMPPLALASP (SEQ ID NO:28), (LRGS)MPPLALASP (SEQ ID NO:29) and HLP-KPANPFPLD (SEQ ID NO:30), wherein the amino acid residue(s) shown in round parentheses is(are) optionally present. In certain embodiments, the linker comprises a sequence selected from the group consisting of PKPAN (SEQ ID NO:31), RARPLN (SEQ ID NO:32); PMPPLA (SEQ ID NO:33) or PPPRP (SEQ ID NO:34). In certain embodiments, the linkers as described herein further comprise a ZC linker sequence at their N-terminal ends. In other embodiments, the linker is includes modifications at the junction with the cleavage domain (FokI), for example as shown in FIGS. 4, 7, 9, 11, 12, 13, 15 and 16.

In still further aspects, described herein is a fusion protein comprising a DNA-binding domain, a modified FokI cleavage domain and a ZC linker between the DNA-binding domain and the FokI cleavage domain. The FokI cleavage domain may be modified in any way, including addition, deletion and/or substitution of one or more amino acids residues. In certain embodiments, the modifications to the FokI cleavage domain comprises one or more additions, deletions and/or substitutions to the N-terminal region of FokI (residues 158-169 of SEQ ID NO:1), including, for example, addition, deletion and/or substitution of 1, 2, 3, 4 amino acid residues. In certain embodiments, the modified FokI cleavage domain comprises deletions of 1, 2, 3, 4 or more amino acids from the N-terminal region of FokI (e.g., deletion of one or more of residues 158, 159, 160 and/or 161 of the wild-type FokI domain of SEQ ID NO:1). In other embodiments, the modified FokI cleavage domain comprises one or more deletions from, and one or more substitutions within, the N-terminal region of FokI (e.g., deletion of one or more of residues 158-161 and substitution of one or more of the remaining residues). In other embodiments, the modified FokI cleavage domain comprises one or more substitutions in the N-terminal region of FokI. In still further embodiments, the modified FokI cleavage domain comprises one or more additional amino acid residues (e.g., 1, 2, 3, 4 or more)N-terminal to the N-terminal-most residue of FokI (residue 158 of SEQ ID NO:1). In other embodiments, the modified FokI cleavage domain comprises one or more additional amino acid residues (e.g., 1, 2, 3, 4 or more)N-terminal to the N-terminal-most residue of FokI (residue 158 of SEQ ID NO:1) and/or one or more substitutions within the N-terminal region of FokI. In certain embodiments, the fusion protein comprises a modified FokI cleavage domain as shown in FIG. 15 or FIG. 16. In other embodiments, the fusion protein comprises a modified FokI cleavage domain as shown in FIG. 15 or FIG. 16 and further comprising one or more modifications within the N-terminal as shown in U.S. Patent Publication No. 20090305419.

In another aspect, described herein is a dimer comprising at least two fusion proteins, each fusion protein comprising a DNA-binding domain, linker and cleavage domain. In certain embodiments, at least one fusion protein comprises a linker as described herein. In other embodiments, both fusion proteins comprise a linker as described herein. In still further embodiments, the DNA-binding domains of the dimer target sequences (e.g., in double-stranded DNA) separated by 5, 6, 7, 8, 9, 10, 11, 12, 13, 14, 15, 16 (or more) base pairs, preferably 5 to 8 base pairs. Any of the fusion proteins may comprise wild-type or engineered cleavage domains.

In another aspect, fusion polypeptides comprising a DNA-binding domain (e.g., a zinc finger or TALE DNA-binding domain), a cleavage half-domain and a linker as described herein are provided.

In another aspect, polynucleotides encoding any of the linkers or fusion proteins as described herein are provided. In some embodiments, the polynucleotides are RNAs.

In yet another aspect, cells comprising any of the polypeptides (e.g., fusion polypeptides) and/or polynucleotides as described herein are also provided. In one embodiment, the cells comprise a pair of fusion polypeptides, each comprising a cleavage domain as disclosed herein.

In yet another aspect, methods for targeted cleavage of cellular chromatin in a region of interest; methods of causing homologous recombination to occur in a cell; methods of treating infection; and/or methods of treating disease are provided. The methods involve cleaving cellular chromatin at a predetermined region of interest in cells by expressing a pair of fusion polypeptides, at least one of which comprises a linker as described herein. In certain embodiments, one fusion polypeptide comprises a linker as described herein and in other embodiments, both fusion polypeptides comprise a linker as described herein. Furthermore, in any of the methods described herein, the pair of fusion polypeptides cleaves the targeted region when the binding sites for the zinc finger nucleases are 5, 6, 7, 8, 9, 10, 11, 12, 13, 14, 15, 16 or even more base pairs apart.

The polypeptides comprising the linkers as described herein can be used in methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof.

A fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

Accordingly, in another aspect, a method for cleaving cellular chromatin in a region of interest can comprise (a) selecting a first sequence in the region of interest; (b) engineering a first DNA-binding domain to bind to the first sequence; (c) expressing a first fusion protein in the cell, the first fusion protein comprising the first DNA-binding domain (e.g., zinc finger or TALE), and a cleavage half-domain; and (d) expressing a second fusion protein in the cell, the second fusion protein comprising a second DNA-binding domain, and a second cleavage half-domain, wherein at least one of the fusion proteins comprises a linker as described herein, and further wherein the first fusion protein binds to the first sequence, and the second fusion protein binds to a second sequence located between 2 and 50 nucleotides from the first sequence, such that cellular chromatin is cleaved in the region of interest. In certain embodiments, both fusion proteins comprise a linker as described herein.

In other embodiments, the disclosure provides methods of cleaving cellular chromatin by introducing one more nucleases comprising a linker as described herein into a cell such that the nucleases target and cleave the cellular chromatin of the cell. The nuclease may comprise a zinc finger nuclease (ZFN), a TALE-nuclease (TALEN), TtAgo or a CRISPR/Cas nuclease system or a combination thereof. The nuclease(s) may be introduced into the cell in any form, for example in protein form, in mRNA form or carried on a viral (AAV, IDLV, etc.) vector or non-viral vector (e.g., plasmid). In certain embodiments, the methods comprise (a) selecting first and second sequences in a region of interest, wherein the first and second sequences are between 2 and 50 nucleotides apart; (b) engineering a first DNA-binding domain to bind to the first sequence; (c) engineering a second DNA-binding domain to bind to the second sequence; (d) expressing a first fusion protein in the cell, the first fusion protein comprising the first engineered DNA-binding domain, a first linker as described herein, and a first cleavage half domain; (e) expressing a second fusion protein in the cell, the second fusion protein comprising the second engineered DNA-binding domain, a second linker and a second cleavage half-domain; wherein the first fusion protein binds to the first sequence and the second fusion protein binds to the second sequence, thereby cleaving the cellular chromatin in the region of interest. In certain embodiments, the first and second fusion proteins comprise a linker as described herein.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated Virus (AAV). Donor sequences can range in length from 10 to 1,000 nucleotides (or any integral value of nucleotides therebetween) or longer. In some embodiments, the donor comprises a full length gene flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments the donor comprises sequences encoding a regulatory element that binds to and/or modulates expression of a gene of interest. In other embodiments, the donor is a regulatory protein of interest (e.g. ZFP TFs, TALE TFs or a CRISPR/Cas TF) that binds to and/or modulates expression of a gene of interest.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end-joining.

In any of the methods described herein in which a pair of nucleases is used, the first and second nucleases of the nuclease pair can bind to target sites 2, 3, 4, 5, 6, 7, 8, 9, 10, 11, 12, 13, 14, 15, 16, 17, 18, 19, 20 or more base pairs apart. In addition, in any of the methods, the second zinc finger binding domain may be engineered to bind to the second sequence.

Furthermore, in any of the methods described herein, the fusion proteins may be encoded by a single polynucleotide.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells.

In another aspect, described herein is a kit comprising a linker as described herein or a polynucleotide encoding a linker as described herein; ancillary reagents; and optionally instructions and suitable containers. The kit may also include one or more nucleases or polynucleotides encoding such nucleases.

In any of the proteins, methods and kits described herein, the cleavage domain (or cleavage half-domain) may comprise a TypeIIS cleavage domain, such as a cleavage half-domain from FokI.

These and other aspects will be readily apparent to the skilled artisan in light of disclosure as a whole.

BRIEF DESCRIPTION OF THE DRAWINGS

FIG. 1 depicts the sequence of an exemplary zinc finger nuclease that binds to a target site in CCR5 (SEQ ID NO:1). The zinc finger DNA binding domain is doubly underlined. The entire FokI cleavage domain is underlined and the N-terminal region is underlined and bolded. A "ZC" linker (LRGS; SEQ ID NO:35) is shown in plain text between the zinc finger and cleavage domains.

FIG. 2A shows host ZFN used in the bacterial selection assay (Example 3, SEQ ID NOs:52-55, respectively, in order of appearance), indicating the location of the randomized linker library. The zinc finger protein domain used for selections included the recognition helices regions of ZFP 8196 as depicted in U.S. Pat. No. 7,951,925, which binds to the CCR5 gene. FIG. 2B is a schematic showing an overview of the bacterial system used for selection of linkers.

FIG. 3 shows an overview of the target sequences (including indicated spacings between target sites) used in the bacterial ccdB toxin plasmid of the bacterial selection system (SEQ ID NOs:56-61, respectively, in order of appearance).

FIG. 4 depicts exemplary linkers obtained from bacterial selections using libraries of 8 to 17 amino acid long linkers for the indicated target spacings (SEQ ID NOs:62-226, respectively, in order of appearance (top to bottom, left to right)). "×2" and "×7" indicate the number of times the sequence was found in the screen.

FIG. 5 shows the distribution of the linker length (8 to 17 amino acids) relative to target spacing (5 to 16 base pairs) after selection.

FIG. 8 is a summary of results obtained with all linkers tested for the indicated target site gaps.

FIGS. 9A through 9C, show ZFN activity and dimer gap preference results. FIGS. 9A and 9B show the results of ZFN-modifications ("indels") obtained with the indicated linkers (SEQ ID NOs:233, 2-6, 234, 161, 235, 233, 7-11, 236, 12-16, 115, 237, 17-21, 238-240 and 71, respectively, in order of appearance) at the indicated gaps between the paired target sites. FIG. 9C shows dimer gap preferences of the indicated linkers.

FIGS. 10A and 10B, shows the design, assembly scheme, and results of portability studies conducted with various linkers. FIG. 10A shows the design of the vectors used, including nucleotide sequences (SEQ ID NOs:241, 243, 245, 247, 249, 251, 253, 257 and 255, respectively, in order of appearance) and amino acid sequences (SEQ ID NOs: 242, 244, 246, 248, 250, 252, 254, 256 and 256, respectively, in order of appearance). Solid blocks labeled 'A', 'B' and 'C" indicate zinc finger modules. FIG. 10B depicts a summary of the results obtained.

FIGS. 11A and 11B, show the activity of linkers) selected to recognize an 8 or 9 bp gap between the target sites. FIG. 11A depicts gels showing the Cel-I results for 8 pairs of ZFNs modified by 4 different linkers. Lanes are numbered according to the Group shown at the bottom of the figure. GFP indicates the GFP expression vector control. An 'X' over the lane indicates a faulty run. FIG. 11B indicates the percent NHEJ activity from the Cel 1 gels in FIG. 11A. FIGS. 11A and B disclose SEQ ID NOS 45 and 45-49, respectively, in order of appearance.

FIG. 13 shows activity of the indicated shows activity (% NHEJ) of the indicated linkers in the indicated zinc finger and cleavage domain vectors (SEQ ID NOs:271-279, respectively, in order of appearance). As shown the linker sequence extends from the amino acid residue immediately C-terminal to the $2^{nd}$ histidine residue of the ZFP sequence to the amino acid residue immediately N-terminal to the EL FokI sequence.

FIG. 15 shows activity (% NHEJ) of ZFNs including linkers as described herein and including modified junctions as between the linker and cleavage domain (in the left and/or right ZFNs of the pair as indicated) (SEQ ID NOs:280-303 and 51, respectively, in order of appearance).

FIG. 16 shows activity (% NHEJ) of different ZFNs including linkers as described herein and including modified junctions as between the linker and cleavage domain (in the left and/or right ZFNs of the pair as indicated). The linker portion of the sequences extends from the amino acid residue immediately C-terminal to the 2nd histidine residue of the ZFP sequence to the amino acid residue immediately N-terminal to the EL FokI sequence. The activities of the ZFN pairs with both conventional junction sequences are boxed. FIG. 16 discloses "GSKS," "GSVKS," "GSEVKS," "GSQSVKS," "GSKQLVKS," "GSGKQLVKS," "GSVT-KQLVKS," "GSQLVKS" and "GSTKQLVKS" as SEQ ID NOS 304-312, respectively.

DETAILED DESCRIPTION

Figure 2A:
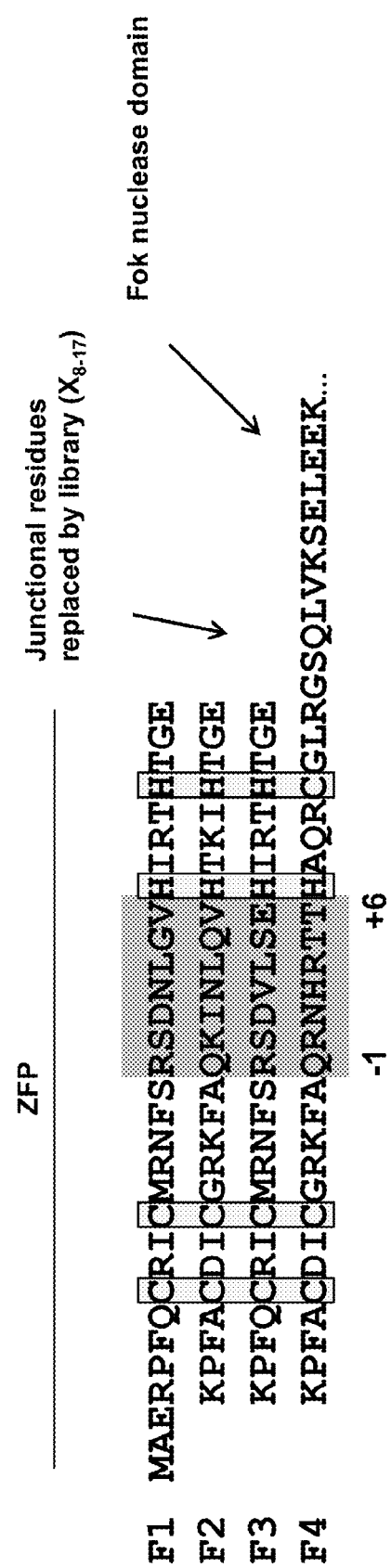
FIGS. 2A and 2B, depict library design and selection.

Described herein are compositions for linking DNA-binding domains and cleavage domains to form artificial nucleases and methods of using these nucleases for targeted alteration of a cellular nucleotide sequence, e.g., by targeted cleavage followed by non-homologous end joining; by targeted cleavage followed by homologous recombination between an exogenous polynucleotide (comprising one or more regions of homology with the cellular nucleotide sequence) and a genomic sequence; by targeted inactivation of one or more endogenous genes.

Exemplary linkers as shown FIGS. 4 and 9 increase the ability of a pair of ZFNs to cleave when the ZFN target sites are more than 5 or 6 base pairs apart. Thus, certain linkers described herein significantly increase the ability to perform targeted genomic alteration by increasing the cleavage activity when the zinc finger target sites are not separated by 5 or 6 base pairs.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; and 6,200,759; WO 95/19431; WO 96/06166; WO 98/53057; WO 98/54311; WO 00/27878; WO 01/60970 WO 01/88197, WO 02/099084 and U.S. Publication No. 20110301073.

"TtAgo" is a prokaryotic Argonaute protein thought to be involved in gene silencing. TtAgo is derived from the bacteria *Thermus thermophilus*. See, e.g. Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598 and U.S. Publication No. 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, DC; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, DC; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. "Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule, a malfunctioning version of a normally-functioning endogenous molecule or an ortholog (functioning version of endogenous molecule from a different species).

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Gene inactivation refers to any reduction in gene expression as compared to a cell that does not include a ZFP as described herein. Thus, gene inactivation may be partial or complete.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site (e.g., 1 to 500 base pairs or any value therebetween on either side of the target site).

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

Additional pairs of zinc-finger proteins, TALENs, TtAgo or CRIPSR/Cas systems can be used for additional double-stranded cleavage of additional target sites within the cell.

In any of the methods described herein, additional pairs of zinc-finger proteins, TALENs, TtAgo or CRIPSR/Cas systems can be used for additional double-stranded cleavage of additional target sites within the cell.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Linkers

Described herein are amino acid sequences that fuse (link) a DNA binding domain (e.g., zinc finger protein, TALE, etc.) and a nuclease (e.g., a cleavage domain or cleavage half-domain).

Currently, when a pair of nucleases is used to cleave a genomic sequence, optimal cleavage is obtained when the DNA-binding proteins bind to target sites separated by less than 6 base pairs. In particular, optimal cleavage for zinc finger nuclease pairs is obtained when the target sites are separated by 5-6 base pairs and a flexible "ZC" linker rich in glycine and serine is used to join each zinc finger of the pair to the cleavage domain. In particular, the "ZC" linker used to date consists of the amino acid sequence LRGS (SEQ ID NO:35) between the C-terminal of the zinc finger binding domain and the N-terminal residues of the cleavage domain, which in the case of FokI is a Q residue. See, e.g., U.S. Pat. No. 7,888,121. In addition, fusion proteins comprising ZC linkers and additional modifications to the N-terminal region of the cleavage domain have also been described. See, U.S. Patent Publication No. 20090305419. Furthermore, U.S. Pat. No. 8,772,453 describes linkers useful for obtaining cleavage when the DNA-binding sites target sequences separated by less than 5 base pairs.

The linkers described herein allow cleavage when the target sites of a pair of zinc finger nucleases are not 0-6 base pairs apart, for example target sites that are 7, 8, 9, 10 or more base pairs apart. The linker sequences described herein are typically between about 8 and 17 amino acids in length and may link the N- or C-terminal of the DNA-binding domain to the N- or C-terminal of cleavage domain. In certain embodiments, the linker extends between the C-terminal residue of the DNA-binding domain and the N-terminal residue of the cleavage domain (e.g., (Q) of FokI).

Non-limiting examples of linkers as described herein are shown in FIGS. 4, 7, 9, 11, 12, 13, 15 and 16 (SEQ ID NOs: 2-21, 45-49, 51, 62-226, 233-240, and 258-312) (with or without 1 or 2 of the C-terminal amino acid residues shown in these Figures), including but not limited to (N)GICPP-PRPRTSPP (SEQ ID NO:2); (T)GTAPIEIPPEVYP (SEQ ID NO:3); (N)GSYAPMPPLALASP (SEQ ID NO:4); (P)GI-YTAPTSRPTVPP (SEQ ID NO:5); (N)GSQTP-KRFQPTHPSA (SEQ ID NO:6); (H)LPKPANPFPLD (SEQ ID NO:7); (H)RDGPRNLPPTSPP (SEQ ID NO:8); (H)RLPDSPTALAPDTL (SEQ ID NO:9); (DPNS)PIS-RARPLNPHP (SEQ ID NO:10); (Y)GPRPTPRLRCPID-SLIFR (SEQ ID NO:11); (H)CPASRPIHP (SEQ ID NO:12); (G)LQSLIPQQLL (SEQ ID NO:13); (G)LQPTVNHEYNN (SEQ ID NO:14); (P)ANIHSLSSPPPL (SEQ ID NO:15); (P)AGLNTPCSPRSRSN (SEQ ID NO:16); (A)TITDPNP (SEQ ID NO:17); (P)PHKGLLP (SEQ ID NO:18); (S)VS-LPDTHH(SEQ ID NO:19); (G)THGATPTHSP (SEQ ID NO:20); (V)APGESSMTSL (SEQ ID NO:21), (LRGS)PIS-RARPLNPHP (SEQ ID NO:22), (LRGS)ISRARPLNPHP (SEQ ID NO:23), (LRGS)PSRARPLNPHP (SEQ ID NO:24), (LRGS)SRARPLNPHP (SEQ ID NO:25), (LRGS)YAPMPPLALASP (SEQ ID NO:26), (LRGS)APMPPLA-LASP (SEQ ID NO:27), (LRGS)PMPPLALASP (SEQ ID NO:28), (LRGS)MPPLALASP (SEQ ID NO:29) HLPK-PANPFPLD (SEQ ID NO:30), wherein the amino acid residue(s) shown in round parentheses is(are) optionally present. In certain embodiments, the linker comprises a sequence selected from the group consisting of PKPAN (SEQ ID NO:31), RARPLN (SEQ ID NO:32); PMPPLA (SEQ ID NO:33) or PPPRP (SEQ ID NO:34). In certain embodiments, the linkers further comprise a ZC linker (LRGS, SEQ ID NO:35) at their N-terminal.

Figure 7:
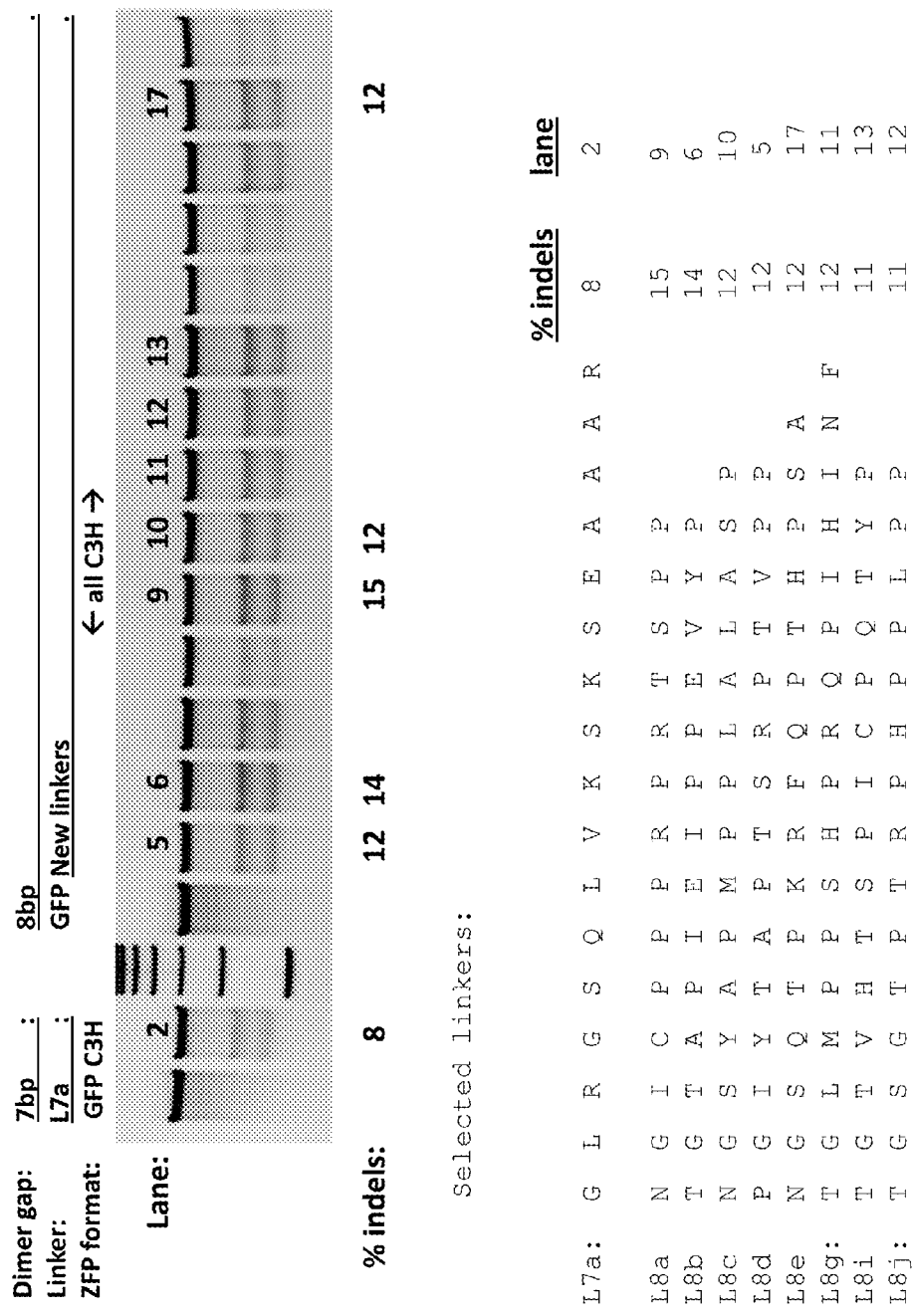
FIG. 7 depicts results of ZFN cleavage with an 8 base pair gap between target sites using the indicated linkers (SEQ ID NOs:233, 2-6, 234, 161 and 235, respectively, in order of appearance).
Figure 9B:
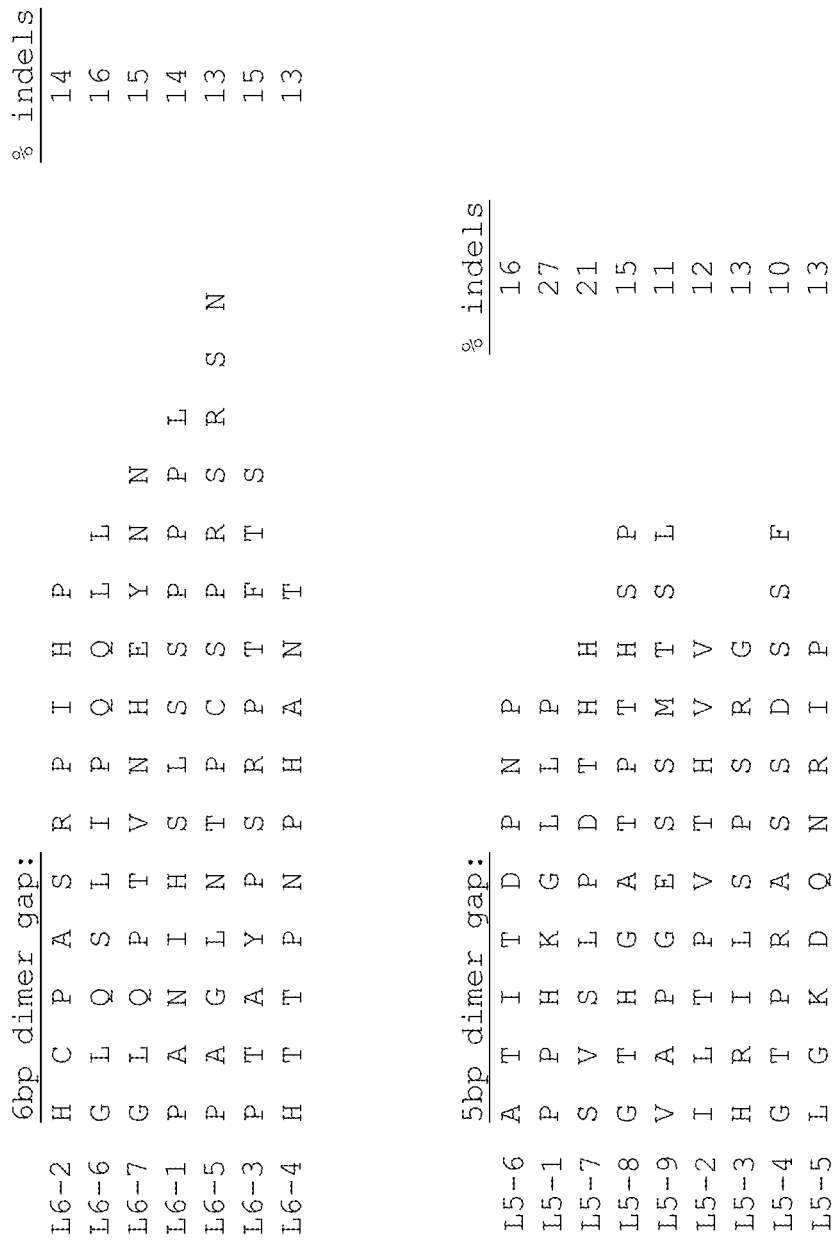

In certain embodiments, the linker comprises a sequence as shown in FIG. 4 (SEQ ID NOs:62-226, respectively, in order of appearance). In other embodiments, the linker comprises a sequence as shown in FIG. 7, FIG. 9A (top), FIG. 12 and FIG. 13 (L8 linkers including, for example, L8a (SEQ ID NO: 2), L8b (SEQ ID NO: 3), L8c (SEQ ID NO: 4), L8d (SEQ ID NO: 5), L8e (SEQ ID NO: 6), L8g (SEQ ID NO: 234), L8i (SEQ ID NO: 161), L8j (SEQ ID NO: 235), L8a (SEQ ID NO: 2), L8c (SEQ ID NO: 4), L8a3 (SEQ ID NO: 268) and L8c3 (SEQ ID NO: 269),). In certain embodiments, the L8 linkers are used when the DNA-binding domains of the dimerizing nuclease pair used for cleavage bind to target sites separate by 8 base pairs. In other embodiments, the linker comprises a sequence as shown in FIG. 9A (bottom), FIG. 12 and FIG. 13 (L7 linkers including, for example, L7-1 (SEQ ID NO: 7), L7-2 (SEQ ID NO: 8), L7-6 (SEQ ID NO: 9), L7-3 (SEQ ID NO: 10), L7-5 (SEQ ID NO: 11), L7-4 (SEQ ID NO: 236), L7-b (SEQ ID NO: 258), L7-c (SEQ ID NO: 259), L7-b3 (SEQ ID NO: 266) and L7-c3 (SEQ ID NO: 267),). In certain embodiments, the L7 linkers are used when the DNA-binding domains of the dimerizing nuclease pair used for cleavage bind to target sites separate by 7 base pairs. In other embodiments, the linker comprises a sequence as shown in FIG. 9B (top) (L6 linkers, including, for example, L6-2 (SEQ ID NO: 12), L6-6 (SEQ ID NO: 13), L6-7 (SEQ ID NO: 14), L6-1 (SEQ ID NO: 15), L6-5 (SEQ ID NO: 16), L6-3 (SEQ ID NO: 115), or L6-4 (SEQ ID NO: 237),). In certain embodiments, the L6 linkers are used when the DNA-binding domains of the dimerizing nuclease pair used for cleavage bind to target sites separate by 6 base pairs. In still other embodiments, the linker comprises a sequence as shown in FIG. 9B (bottom) (L5-6 (SEQ ID NO: 17), L5-1 (SEQ ID NO: 18), L5-7 (SEQ ID NO: 19), L5-8 (SEQ ID NO: 20), L5-9 (SEQ ID NO: 21), L5-2 (SEQ ID NO: 238), L5-3 (SEQ ID NO: 239), L5-4 (SEQ ID NO: 240), L5-5 (SEQ ID NO: 71),). In certain embodiments, the L5 linkers are used when the DNA-binding domains of the dimerizing nuclease pair used for cleavage bind to target sites separate by 5 base pairs.

Figure 2B:
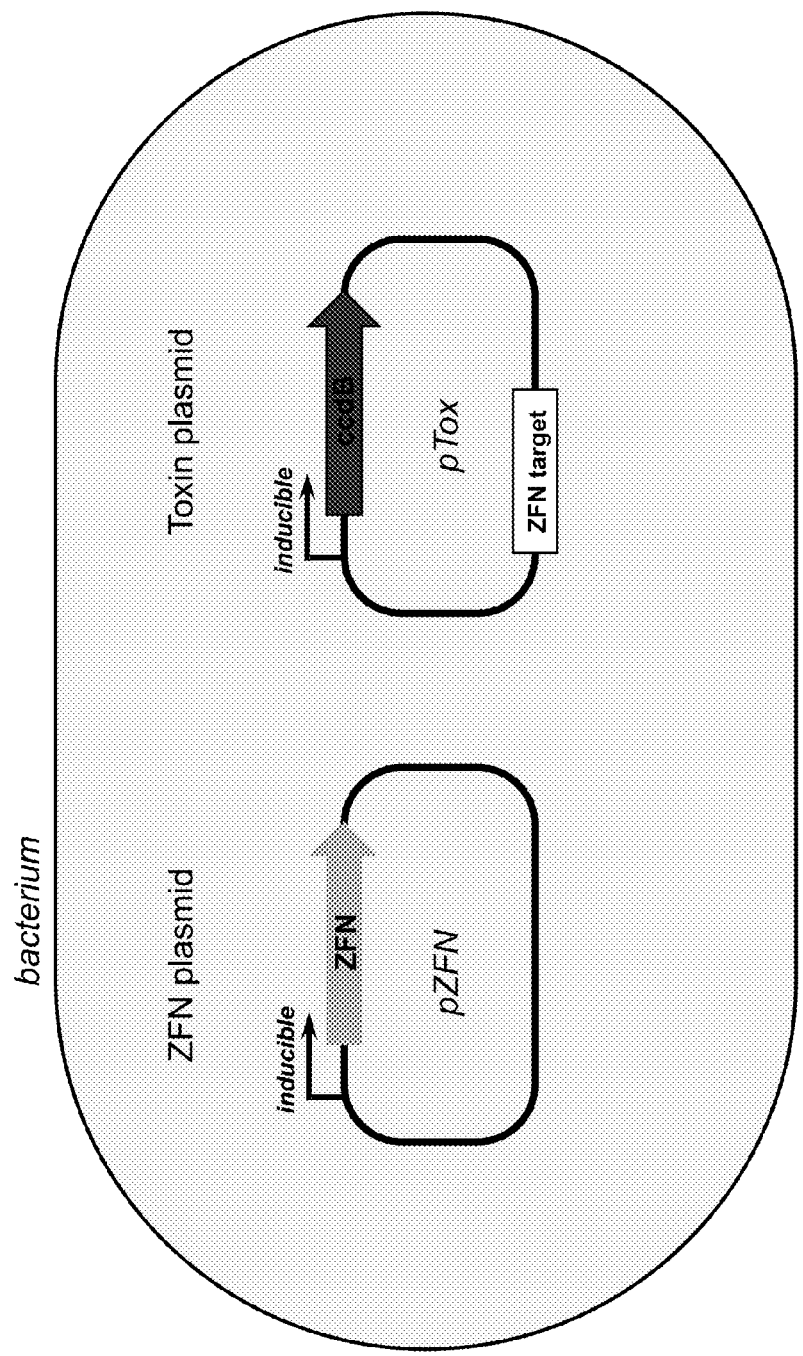

The fusion proteins described herein may also include alterations to the N-terminal region of the selected cleavage domain. Alteration may include substitutions, additions and/or deletions of one or more N-terminal residues of the cleavage domain. In certain embodiments, the cleavage domain is derived from FokI and one or more amino acids of the wild-type FokI N-terminal region are replaced and additional amino acids added to this region. For example, as shown in FIG. 2, amino acid residues 4 and 5 of the wild-type FokI cleavage domain (i.e., residues K and S) are replaced with residues E and A, respectively and the residues AAR is added C-terminal to the $2^{nd}$ replaced residue. Another exemplary embodiment (FIG. 3) includes a seven residue insertion (KSEAAAR; SEQ ID NO:36) in the N-terminal region of the FokI cleavage domain.

The sequence joining the DNA-binding domain and the cleavage domain can comprise any amino acid sequence that does not substantially hinder the ability of the DNA-binding domain to bind to its target site or the cleavage domain to dimerize and/or cleave the genomic sequences. In wild-type FokI, the N-terminal region of the cleavage domain includes an alpha helical region extending from residues 389-400 (ELEEKKSELRHK; SEQ ID NO:37). See, e.g., Wah et al. (1997) Nature 388:97-100). Therefore, in certain embodiments, the linker sequences are designed to extend and/or conserve this structural motif, for example by inserting a 3-5 amino sequence N-terminal to ELEEKKSELRHK (SEQ ID NO:37) of a wild-type FokI cleavage domain.

Thus, the linker may include a sequence such as EXXXR (SEQ ID NO:38) or EXXXK (SEQ ID NO:39) where the X residues are any residues that form an alpha helix, namely any residue except proline or glycine (e.g., EAAAR (SEQ ID NO:40)) adjacent to the wild-type alpha helical region to form a stable alpha helix linker. See, e.g., Yan et al. (2007) Biochemistry 46:8517-24 and Merutka and Stellwagen (1991) Biochemistry 30:4245-8. Placing an EXXXR (SEQ ID NO:38) or EXXXK (SEQ ID NO:39) peptide adjacent (or near to) to the ELEEKKSELRHK (SEQ ID NO:37) peptide is designed to extend this alpha helix in FokI cleavage domain. This creates a more rigid linker between the ZFP and FokI cleavage domain which allows the resulting ZFN pair to cleave a target with more than 6 bp between the half sites without the loss in activity and specificity that can be observed when a long flexible linker is used between the ZFP and the FokI domain (Bibikova et al. (2001) Molecular and Cellular Biology 21:289-297). In addition, the linkers described herein show a greater preference for a 6 bp spacing over a 5 bp spacing as compared to current ZFNs.

Furthermore, in certain embodiments, the junction as between the linker and the cleavage domain and/or DNA-binding domain is modified, for example to substitute, add and/or delete amino acids to the linkers as described herein. In certain embodiments, 1, 2, 3, 4 or more amino acids are deleted or added. In other embodiment, 1, 2 or 3, 4 amino acid substitutions are made. Non-limiting examples of modified linkers as described herein are shown in FIGS. 15 and 16 (SEQ ID NOs:280-312 and 51).

Also described herein is a fusion protein comprising a DNA-binding domain, a modified FokI cleavage domain and a ZC linker between the DNA-binding domain and the FokI cleavage domain. The FokI cleavage domain may be modified in any way. Non-limiting examples of modifications include additions, deletions and/or substitutions to the N-terminal region of FokI (residues 158-169 of SEQ ID NO:1). In certain embodiments, the modified FokI cleavage domain comprises deletion of 1, 2, 3, 4 or more amino acids from the N-terminal region of FokI (e.g., deletion of one or more of residues 158, 159, 160 and/or 161 of the wild-type FokI domain of SEQ ID NO:1). Non-limiting examples of proteins with deletions of N-terminal FokI amino acid residues include the proteins designated V1, V3 and V7 as shown in FIG. 15. In other embodiments, the modified FokI cleavage domain comprises one or more deletions and one or more substitutions from the N-terminal region of FokI (e.g., deletion of one or more of residues 158-161 and substitution of one or more of the remaining residues). Non-limiting examples of proteins with deletions and substitutions in the N-terminal FokI amino acid residues include the proteins designated V2, V4, V5, V6 and V8 as shown in FIG. 15. In other embodiments, the modified FokI cleavage domain comprises one or more substitutions in the N-terminal region of FokI. Non-limiting examples of proteins with substitutions in the N-terminal amino acid residues of FokI include the proteins designated V9 through V16 as shown in FIG. 15. In still further embodiments, the modified FokI cleavage domain comprises one or more additional amino acid residues (e.g., 1, 2, 3, 4 or more)N-terminal to the N-terminal-most residue of FokI (residue 158 of SEQ ID NO:1). Non-limiting examples of proteins with additions to the N-terminal FokI amino acid residues include the proteins designated V17 through V24 as shown in FIG. 15. In other embodiments, the modified FokI cleavage domain comprises one or more additional amino acid residues (e.g., 1, 2, 3, 4 or more)N-terminal to the N-terminal-most residue of FokI (residue 158 of SEQ ID NO:1) and one or more substitutions within the N-terminal region of FokI. Non-limiting examples of proteins with additions include those shown in FIG. 15 or FIG. 16 and substitutions within the N-terminal FokI amino acid residues as described in U.S. Patent Publication No 20090305419. In certain embodiments, the fusion protein comprises a modified FokI cleavage domain as shown in FIG. 15 or FIG. 16.

Typically, the linkers of the invention are made by making recombinant nucleic acids encoding the linker and the DNA-binding domains, which are fused via the linker amino acid sequence. Optionally, the linkers can also be made using peptide synthesis, and then linked to the polypeptide DNA-binding domains.

Nucleases

The linker sequences described herein are advantageously used to link DNA-binding domains, for example zinc finger proteins, TALEs, homing endonucleases, CRISPR/Cas and/or Ttago guide RNAs, to nuclease cleavage domains or half domains to form specifically targeted, non-naturally occurring nucleases.

A. DNA-Binding Domains

Any DNA-binding domain can be used in the methods disclosed herein. In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Patent Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ('LAGLIDADG' disclosed as SEQ ID NO: 41), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brgll and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et al ((2010)<*Genetics*epub 10.1534/genetics.110.120717). In certain embodiments, TALE domain comprises an N-cap and/or C-cap as described in U.S. Pat. No. 8,586,526. In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TAL-ENs (e.g., one or more TALENs (cTALENs or FokI-TAL-ENs) with one or more mega-TALs).

In certain embodiments, the DNA-binding domain is part of a CRISPR/Cas nuclease system. See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoSComput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as (iii) expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides,* and *Thermus thermophilus.*

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to effect a panopoly of outcomes including gene knock-out, targeted gene addition, gene correction, targeted gene deletion using techniques standard in the art for exploitation of DNA breaks.

B. Cleavage Domains

The nucleases described herein (e.g., ZFNs, TALENs, CRISPR/Cas nuclease) also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., Si Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof).

In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease, or a DNA binding domain from a CRISPR/Cas system and a cleavage domain from a difference nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., Si Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. No. 7,888,121, the disclosure of which is incorporated by reference in its entirety for all purposes.

Cleavage domains with more than one mutation may be used, for example mutations at positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey" mutations (see Guo et al, (2010) *J. Mol. Biol.* 400(1):96-107).

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA-binding domains of the fusion proteins comprising the linkers as described herein can be engineered to bind to any sequence of choice. An engineered DNA-binding domain can have a novel binding specificity, compared to a naturally-occurring DNA-binding domain.

Non-limiting examples of suitable target genes a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFX5 gene, a FAD2 gene, a FAD3 gene, a ZP15 gene, a KASII gene, a MDH gene, and/or an EPSPS gene.

In certain embodiments, the nuclease targets a "safe harbor" loci such as the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Donors

In certain embodiments, the present disclosure relates to nuclease-mediated modification of the genome of a stem cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin. Further, for targeted insertion of sequences not normally present in a region of interest, said sequences can be present in a donor nucleic acid molecule and flanked by regions of homology to sequence in the region of interest.

As with nucleases, the donors can be introduced in any form. In certain embodiments, the donors are introduced in mRNA form to eliminate residual virus in the modified cells. In other embodiments, the donors may be introduced using DNA and/or viral vectors by methods known in the art. See, e.g., U.S. Patent Publication Nos. 20100047805 and 20110207221. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter. The donor molecule may be inserted into an endogenous gene such that all, some or none of the endogenous gene is expressed. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes). Exemplary splice acceptor site sequences are known to those of skill in the art and include, by way of example only, CTGACCTCTTCTCT-TCCTCCCACAG, (SEQ ID NO:42) (from the human HBB gene) and TTTCTCTCCACAG (SEQ ID NO:43) (from the human Immunoglobulin-gamma gene).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to patients.

Methods of delivering nucleases as described herein are described, for example, in U.S. Pat. Nos. 7,888,121; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. Patent Publication No. 20140335063 incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, nanoparticles, polycation or lipid:nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof.

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Kits

Also provided are kits comprising any of the linkers described herein and/or for performing any of the above methods. The kits typically contain a linker sequence as described herein (or a polynucleotide encoding a linker as described herein). The kit may supply the linker alone or may provide vectors into which a DNA-binding domain and/or nuclease of choice can be readily inserted into. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

Applications

The disclosed linkers are advantageously used to link with engineered DNA-binding domains with cleavage domains to form nucleases for cleaving DNA. The linkers as described herein allow for the cleavage of DNA when the target sites of a pair of nucleases used for cleavage are of variable spacings, for example target sites that are not 5 or 6 base pairs apart (e.g., 7, 8, 9 or more base pairs apart). Cleavage can be at a region of interest in cellular chromatin (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele. Such methods are described in detail, for example, in U.S. Pat. No. 7,888,121, incorporated by reference in its entirety herein.

Accordingly, the disclosed linkers can be used in any nuclease for any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, Alsheimer's disease, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, Parkinson's disease, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240) and X-linked SCID.

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, International Patent Publication WO 2007/139982. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Nucleases containing the disclosed linkers can also be used for inactivation (partial or complete) of one or more genomic sequences. Inactivation can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript.

Nuclease-mediated inactivation (e.g., knockout) of endogenous genes can be used, for example, to generate cell lines deficient in genes involved in apoptosis or protein production (e.g., post-translational modifications such as fucosylation). ZFN-mediated inactivation can also be used to generate transgenic organisms (e.g., plants, rodents and rabbits).

In addition, because nucleases don't appear to have specificity for the DNA sequence between the two paired half sites, nucleases with linkers as described herein can be designed to cleave DNA such that the resulting single-stranded overhangs have any desired sequence. In particular, linkers as described herein can be designed to influence both the size and position of these single-stranded overhangs with respect to the starting sequence. Thus, when incorporated into one or more nucleases of a nuclease pair, linkers as described herein can result in more uniform ends following cleavage. Accordingly, the linkers described herein can also be used to more efficiently clone DNA cut with nucleases, which is broadly applicable in many areas of biotechnology and basic science.

Thus, the linkers described herein provide broad utility for improving nuclease-mediated cleavage in gene modification applications. Linkers as described herein may be readily incorporated into any existing nuclease by either site directed mutagenesis or subcloning to be used in many applications in standard cloning, constructing large genomes for synthetic biology, new types of RFLP analysis of large sequences or even allow new types of cloning involving extremely large DNA sequences. The potential properties of nucleases with rigid linkers could also be ideal in applications such as DNA computing.

The following Examples relate to exemplary embodiments of the present disclosure in which the nuclease comprises one or more ZFNs. It will be appreciated that this is for purposes of exemplification only and that other nucleases can be used, for instance TALENs, homing endonucleases (meganucleases) with engineered DNA-binding domains and/or fusions of naturally occurring of engineered homing endonucleases (meganucleases) DNA-binding domains and heterologous cleavage domains, and nuclease systems such as TtAgo and CRISPR/Cas using engineered single guide RNAs.

EXAMPLES

Example 1: Design and Construction of ZFNs with Rigid Linkers

Zinc finger nuclease constructs targeted to the human CCR5 locus were prepared as disclosed in U.S. Pat. No. 7,951,925. "Wild-type constructs" included the "ZC" linker.

In addition, pairs of ZFNs targeted to sequences in the human mitochondria containing the mutation that causes MELAS (mitochondrial myopathy, encephalopathy, lactic acidosis, and stroke) were also prepared to include the L7a or L6a linker as described in U.S. Patent Publication No. 20090305419.

Example 2: ZFN Activity

A. CCR5-Targeted ZFNs

Constructs encoding CCR5-targeted ZFN SBS #8266 were initially tested in a yeast Mel-I reporter system as described in U.S. Pat. No. 8,563,314. In particular, yeast strains having an inverted repeat of the SBS #8266 target site separated by 3, 4, 5, 6, 7, or 8 bp were used to characterize the constructs.

The wild-type ZFN (with the standard LRGSQLVK-SELEEKKS (SEQ ID NO:44) linker showed strong activity with 5 bp and 6 bp half site spacings. In addition, the constructs with the L6a linker sequence (FIG. 2) showed activity at 6p spacings and the L7a linker sequence showed significant activity with 7 bp and 8 bp spacings.

In vitro DNA binding and cleavage activity of the MELAS-targeted ZFNs was also assayed and pairs of ZFNs including the rigid L7a linker cleaved their target.

Finally, the CCR5 ZFNs including the L7a linker were tested for NHEJ activity at the endogenous human CCR5 locus in cell lines that contain various numbers of base pairs between the half sites. Results are shown in Table 1.

TABLE 1

| ZFN | target sites separated by | % NHEJ (exp't #1) | % NHEJ (exp't #2) | % NHEJ (average) |
|---|---|---|---|---|
| Wt ZFNs | 4 bp | 1.2 | 1.1 | 1.2 |
| Wt ZFNs | 5 bp | 36.0 | 34.0 | 35.0 |
| Wt ZFNs | 6 bp | 13.4 | 8.8 | 11.1 |
| Wt ZFNs | 7 bp | 0.0 | 0.0 | 0.0 |
| Wt ZFNs | 8 bp | 0.0 | 0.0 | 0.0 |
| L6a ZFNs | 4 bp | 0.0 | 0.0 | 0.0 |
| L6a ZFNs | 5 bp | 44.4 | 34.1 | 39.3 |
| L6a ZFNs | 6 bp | 26.2 | 24.6 | 25.4 |
| L6a ZFNs | 7 bp | 6.5 | 3.7 | 5.1 |
| L6a ZFNs | 8 bp | 0.0 | 0.0 | 0.0 |
| L7a ZFNs | 4 bp | 0.0 | 0.0 | 0.0 |
| L7a ZFNs | 5 bp | 0.0 | 0.0 | 0.0 |

TABLE 1-continued

| ZFN | target sites separated by | % NHEJ (exp't #1) | % NHEJ (exp't #2) | % NHEJ (average) |
|---|---|---|---|---|
| L7a ZFNs | 6 bp | 33.1 | 30.5 | 31.8 |
| L7a ZFNs | 7 bp | 41.1 | 38.1 | 39.6 |
| L7a ZFNs | 8 bp | 7.9 | 4.6 | 6.1 |

As expected, the wild-type ZFNs only showed high activity at half-sites separated by 5 or 6 bp. However, CCR5-targeted ZFNs including the rigid L7a linker showed high activity with a 7 bp spacing and noticeable activity with the 8 bp spacing. It should be noted that the efficiency of the L7a constructs with the 7 bp spacing is very similar to the efficiency of the wild type ZFNs with a 5 bp spacing (either in the wild-type cell line or a cell line with a different sequence of the 5 bp in between the half sites).

In addition, combinations of linkers were also tested in CCR5-targeted ZFN pairs. Briefly, K562 cells were engineered to have gaps of 4 to 8 base pairs (bp) between the CCR5 ZFN binding sites. Two CCR5 ZFNs with different linkers combinations (Wt/L7a) were transfected into these K562 cells by Amaxa Shuttle. Samples were harvested 3 days after transfection and subjected to CEL1-I assay analysis. CEL-I mismatch assays were performed essentially as per the manufacturer's instructions (Trangenomic SURVEYOR™).

The results indicate that the Wt/Wt linker ZFN has the highest activity with 5 bp gap target sequence; the L7a/L7a linker ZFN had the highest activity with a 7 bp gap sequence, and the ZFNs with Wt/L7a or L7a/Wt linker combinations had the highest activity with a 6 bp gap sequence.

B. ROSA-Targeted ZFNs

Neuro2A cells were transfected with combinations of mROSA-targeted ZFNs (see, e.g., U.S. Patent Publication No. 2007/0134796) by Amaxa Shuttle using a target site with a 6 bp gap. One ZFN of the pairs included a wild-type linker ("ZC") and the other included either wild-type or L7a linker as described herein. Samples were harvested 3 days after transfection and subjected to CEL-I analysis, as described above.

As shown in Table 2 below, the wild type (WT)/L7a linker in a pair of ZFNs is active with a 6 bp gap.

TABLE 2

| Sample | Linker #1 | Linker #2 | % NHEJ |
|---|---|---|---|
| mock transfection (no ZFN) | NA | NA | 0.4 |
| Rosa-ZFN pairs | Wt | Wt | 22.6 |
| Rosa-ZFN pairs | Wt | L7a | 7.5 |
| Rosa-ZFN pairs | Wt | Wt | 23.2 |
| Rosa-ZFN pairs | Wt | Wt | 18.7 |
| GFP-ZFN pairs | Wt | L7a | 5.3 |
| GFP-ZFN pairs | Wt | Wt | 21.5 |

C. Rat IgM

Rat C6 cells were transfected with combinations of rat IgM-targeted ZFNs (see, e.g., U.S. Publication No. 20100218264) by Amaxa Shuttle using a target site with a 6 bp gap. One ZFN of the pairs included a wild-type linker ("ZC") and the other included either wild-type or L7a linker. Samples were harvested 9 days after transfection and subjected to CEL-I analysis, as described above and in U.S. Patent Publication No. 2007/0134796.

Cells containing the pair of ZFNs that included the L7a linkers showed 2.43% NHEJ as compared to cells containing a pair of ZFNs that included the ZC linker, which showed 1.93% NHEJ. Furthermore, the L7a-containing linker ZFN pair was used to inject into rat ES cells (as described in U.S. Publication No. 20100218264) and these ES cells successfully produced homozygous IgM gene knockout rat offspring.

Example 3: Additional Linker Designs

Additional linkers were generated from a bacterial selection system that was modified from Barbas et al. (2010) *J. Mol. Biol.* 400:96-107. Briefly, bacteria were transformed with a ZFN-encoding plasmid (expression of the ZFN driven by the arabinose inducible promoter) and a plasmid that expressed the bacterial ccdB toxin from the T7 promoter and included the ZFN target sites. See, FIG. 2. This system allowed the ability to query very large libraries with complexities of ~$10^8$ and a high stringency option (>100 cleavage events required for survival).

The expressed ZFN cleaved pTox leading to degradation of pTox; the ccdB toxin was then switched on for cell killing; the survivors (ZFN-cleaved pTox) were amplified and the genes encoding the linkers re-cloned into new plasmids for the next cycle. See, FIGS. 2A and 2B. The ZFNs included fully randomized linkers of between 8 and 17 amino acids in length between the zinc finger protein domain and the cleavage (FokI) domain. See, FIG. 2A.

Engineered cleavage domains and canonical (C2H2) and non-canonical finger structures (see, U.S. Patent Publication No. 20080182332) may be used; for this study wild-type FokI domains (which form homodimers) and CCHC finger structures were employed. Linkers were selected on gaps between ZFN target sequences of 5-16 base pairs.

To select for active pZFNs from the vast excess of inactive ones, the following steps were performed: (i) High-complexity DNA libraries were constructed, see FIG. 2A, (ii) plasmid DNA library was transformed into cells bearing pTox_8196-bs; (iii) expressed ZFNs for 2 hours; (iv) induced ccdB overnight; (v) minipreped plasmids and subclone linker DNA into new pZFN; repeated (ii)-(v) for 7 more cycles.

Exemplary functional linkers obtained from the selections are shown in FIG. 4. A summary of the length distribution of the linkers which cleaved at the indicated gaps is shown in FIG. 5.

Example 4: Verifying Activity and Portability Studies

Figure 6:
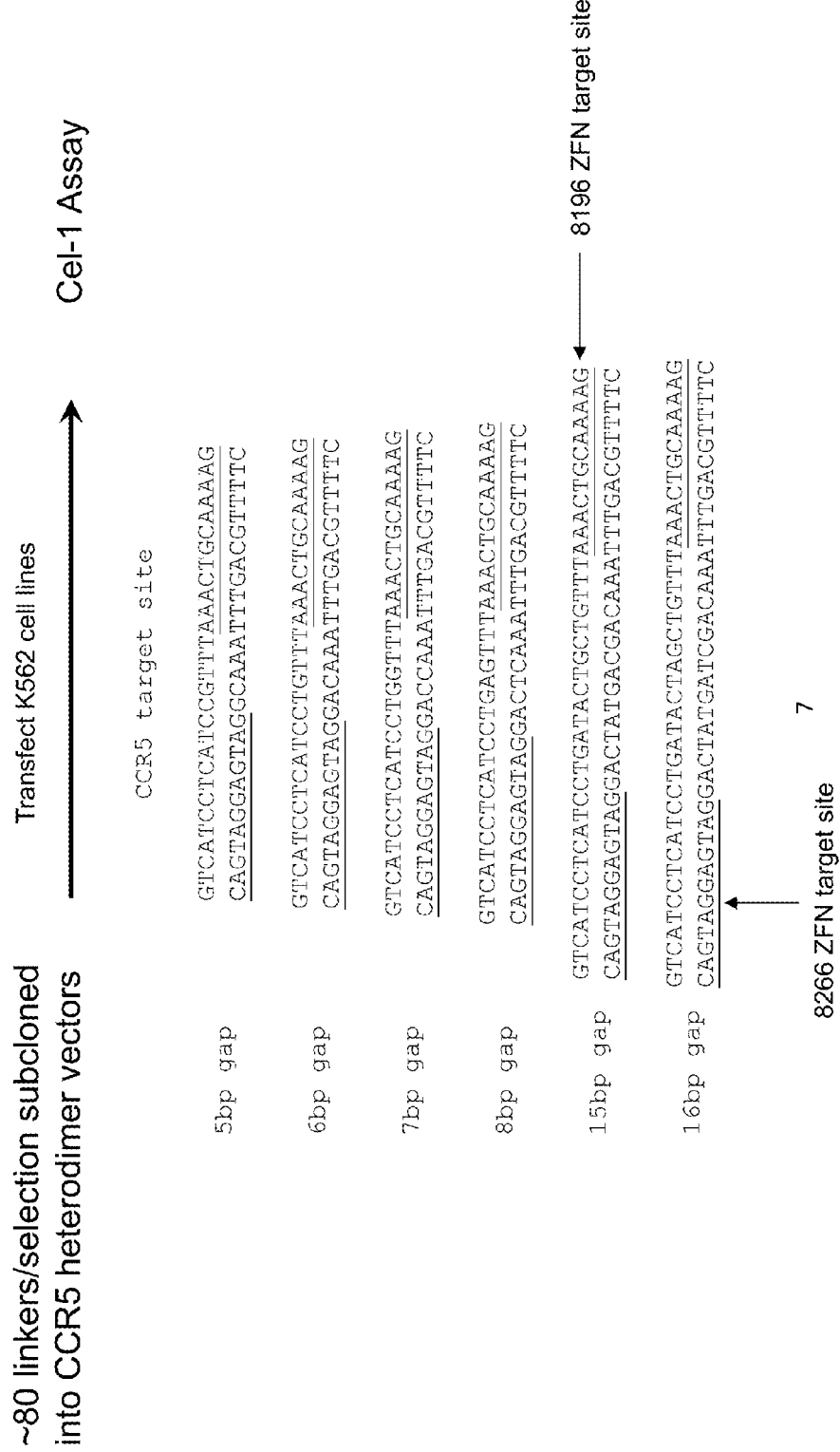
FIG. 6 depicts an overview of the target sites for the modified CCR5 locus in mammalian cells, including target sequences and spacings (SEQ ID NOs:227-232, respectively, in order of appearance).

Selected candidates (ZFNs with linkers) were screened for modification of an endogenous target in six variant K562 cell lines, which were engineered at the CCR5 locus to replace the gap between heterodimeric target sites (8166 and 8266 ZFNs as described in U.S. Pat. No. 7,951,925) with new gaps of 5-16 base pairs (e.g., 5, 6, 7, 8, 15 or 16 bp). Linker cassettes (~80/selection=480 total) were substituted for L0 linkers in CCR5 ZFN expression vectors with the CCHC structure and constructs were transfected into appropriate K562 cells. See, FIG. 6. Activity was assessed using a Cel1 assay, as described above and in U.S. Patent Publication No. 2007/0134796.

Figure 9C:
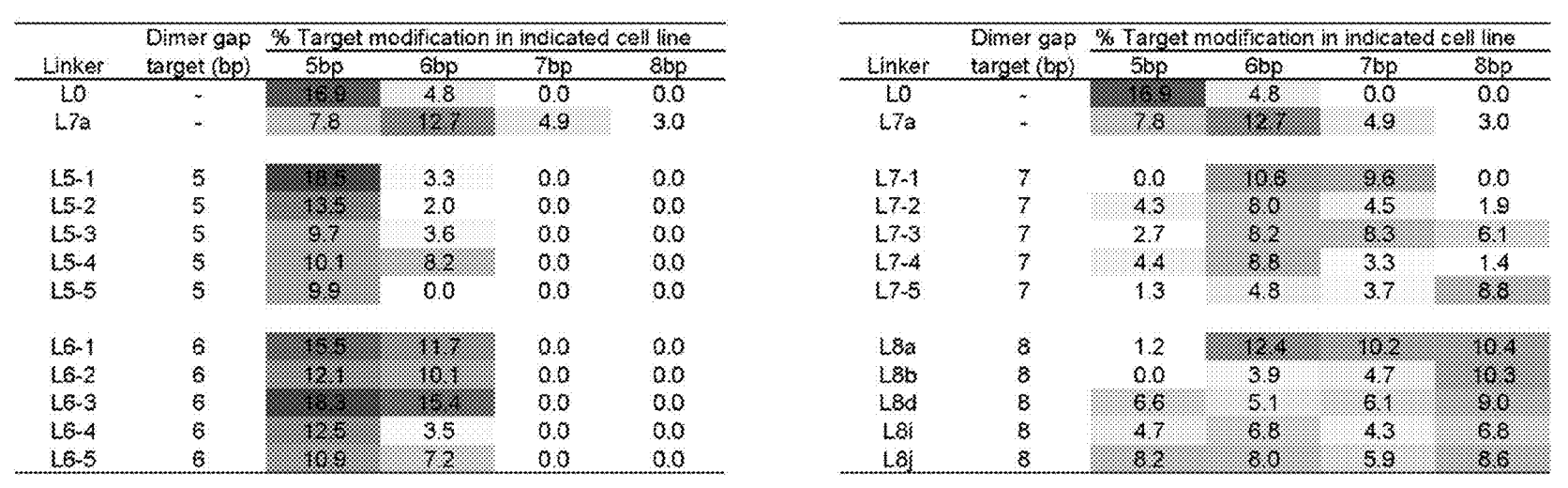

FIG. 8 shows a summary of the results obtained with the selected linkers with the indicated target gaps. FIGS. 9A and 9B show the most active linkers for a 5-8 base pair gap between target sites. "Indels" refers to insertions or deletions, usually small, within the target sequence following ZFN-mediated modification (e.g., following cleavage and NHEJ repair). Linkers were also tested for activity with different gap spacings. FIG. 9C shows the gap preference for the indicated linkers.

Figure 10A:
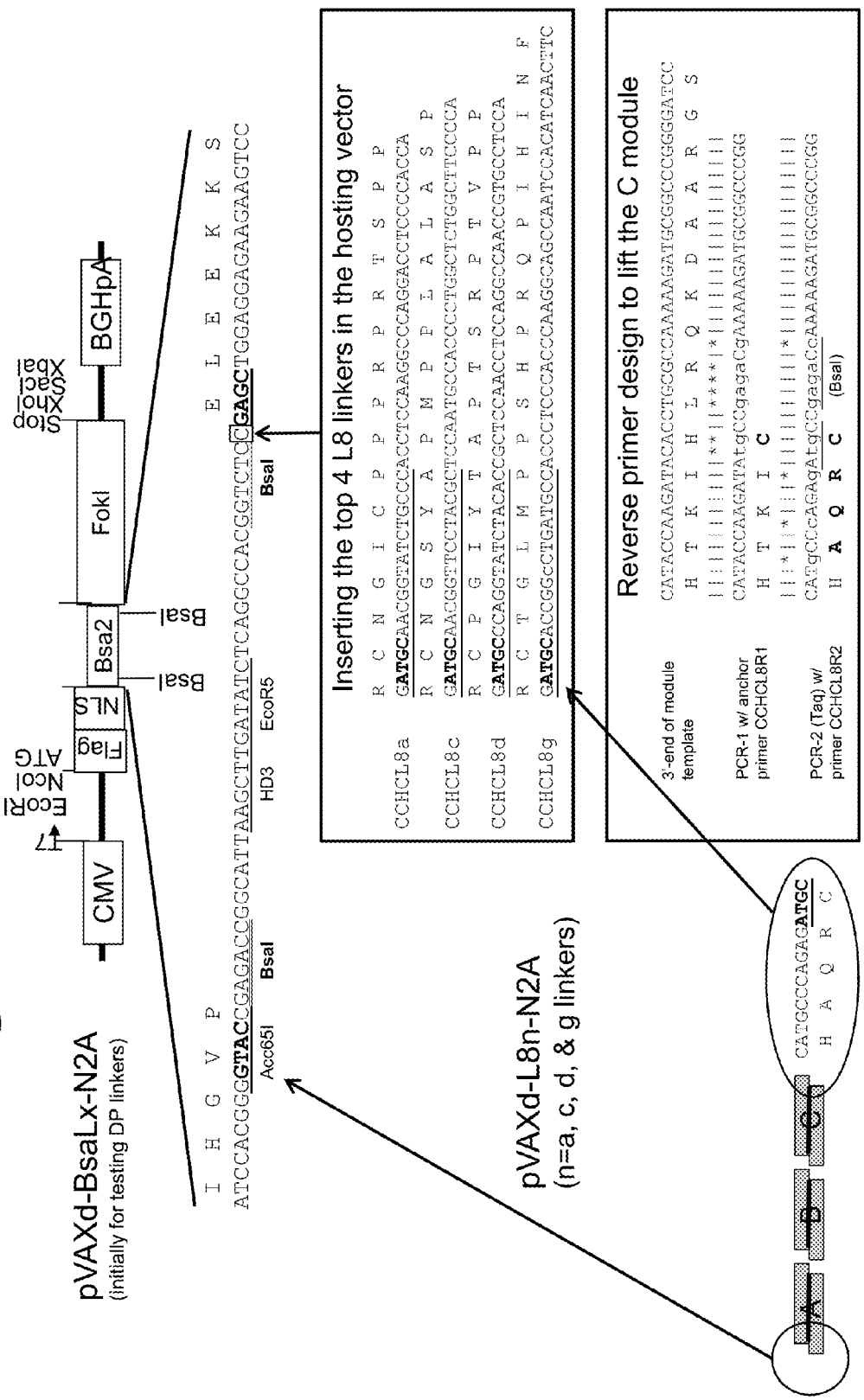
Figure 11A:
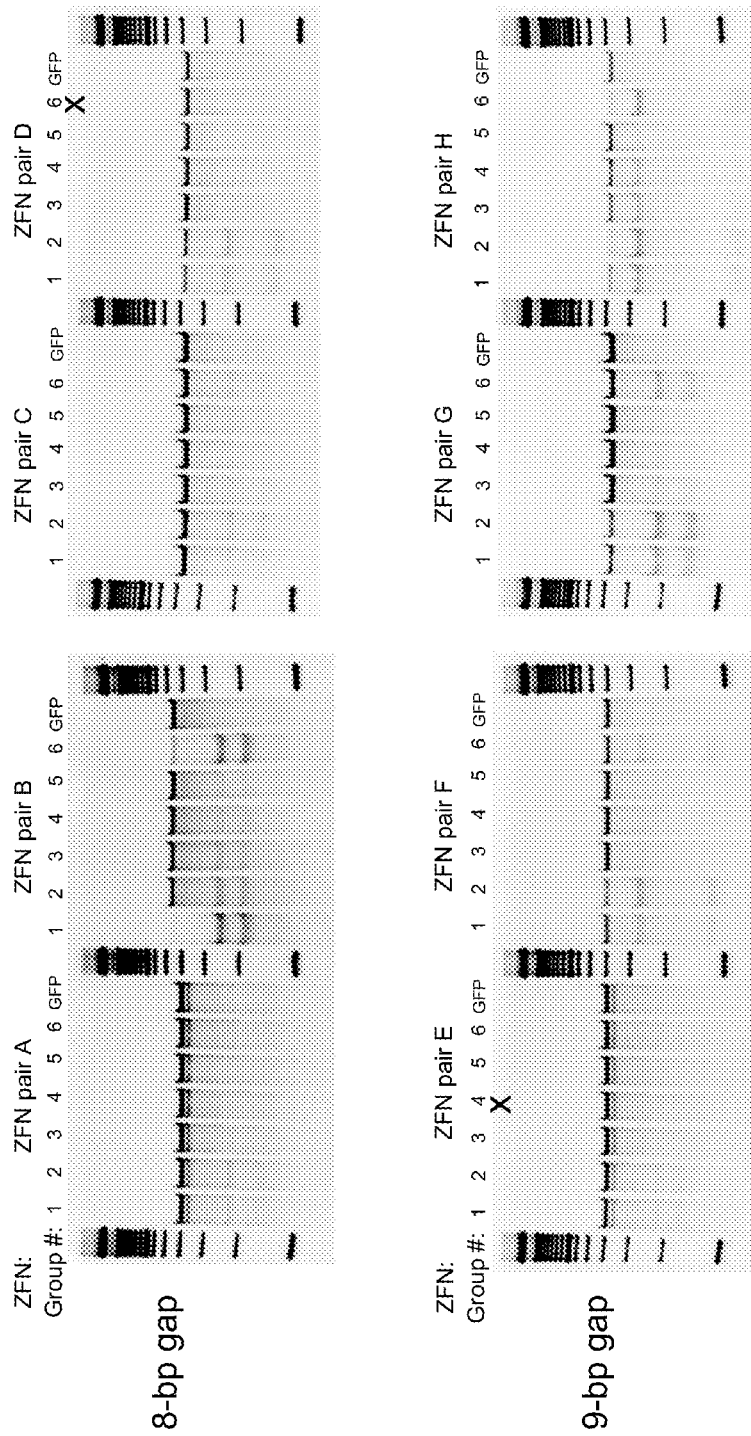

For portability studies, four L8 linkers were chosen for cloning and testing with a large target gene to ensure consistent high design scores for all test sets. A schematic of the vector designs is shown in FIG. 10A. Sets of the 32 ZFNs were generated for each of L0 (5, 6 bp gap), L7a (7 bp gap), and L8 (8 bp gap) linkers for a total of 92 ZFNs. See, FIG. 7 for L8 linkers. Activity was verified by Cel-1 assay, as described above and in U.S. Patent Publication No. 2007/0134796.

FIG. 10B shows a summary of the results of the portability studies and demonstrates many ZFNs tested were active. The number active and level of modification of the selected linkers was comparable to previously used linkers at a 5 or 6 (L0) or 7 bp spacing (L7a).

The L8c linkers were also additionally modified. A different target was chosen and eight pairs of C2H2 ZFNs were used to select for activity for 8 bp (termed A, B, C, D) and 9 bp (termed E, F, G, and H) gaps against their specific targets. The linkers in the ZFN pairs were altered with 4 different linker types (termed L8n, L8o, L8m and L8p) and the pairs were selected for activity against target sites where the gaps between the ZFN binding sites were separated by 8 or 9 bp. Additionally, the original L8c linker was used in the pairs to attach either a wt Fok1 nuclease domain or enhanced obligated heterodimeric Fok1 nuclease domains (eHiFi) for comparison. A GFP expression vector was used as a transfection control. The peptide sequences of the original L8c linker and the 4 modified linkers are shown below (linker sequences underlined):

```
Group 1: L8c
                                     (SEQ ID NO: 45)
[ZFP]HAQRC-NGSYAPMPPLALASPELEEKESEL[wt FokI]

Group 2: L8c
                                     (SEQ ID NO: 45)
[ZFP]HAQRC-NGSYAPMPPLALASPELEEKESEL[eHiFi FokI]

Group 3: L8n
                                     (SEQ ID NO: 46)
[ZFP]HTKIH-NGSYAPMPPLALASPELEEKESEL[eHiFi FokI]

Group 4: L8o
                                     (SEQ ID NO: 47)
[ZFP]HTKIH-GGSYAPMPPLALASPELEEKESEL[eHiFi FokI]

Group 5: L8m
                                     (SEQ ID NO: 48)
[ZFP]HTKIH--GSYAPMPPLALASPELEEKESEL[eHiFi FokI]

Group 6: L8p
                                     (SEQ ID NO: 49)
[ZFP]HTKIHLRGSYAPMPPLALASPELEEKESEL[eHiFi FokI]
```

The results (see FIGS. 11A and 11B) demonstrated that the L8c type linker worked well in both the CCHC and C2H2 ZFP backgrounds. Additionally, the L8p linker worked well with both 8 bp and 9 bp gaps.

Example 5: Further Linker Studies

The "L7a" linker is currently used in as the ZFP-FokI linker to target the 7-bp gap sites in both C2H2 and CCHC ZFP architectures. Linkers shown in FIGS. 9A and 9B were identified within a CCHC ZFP architecture so further studies were conducted in C2H2 architecture of ZFPs that target 7-bp gap sites.

Four linker peptide sequences as shown in FIG. 9A (L7-1, L7-3, L8a, and L8c) were initially selected for these studies, including these linkers with and without one or more optional residues as shown in parentheses as follows: (H)LPKPANPFPLD (SEQ ID NO:7); (D)PNSPISRARPL-NPHP (SEQ ID NO:10); (N)GICPPPRPRTSPP (SEQ ID NO:2); and (N)GSYAPMPPLALASP (SEQ ID NO:4).

A pair of ZFPs that targets a 7-bp gap site was used to test the linkers. This pair of ZFNs was engineered in the context of CCHC or C2H2 architectures, with various linker sequences, and fused to either wild-type ("wt") or enhanced obligated heterodimeric FokI ("eHiFi") domains. See, e.g., U.S. Pat. Nos. 8,623,618; 7,888,121; 7,914,796; and 8,034,598 and U.S. Publication No. 20110201055 for exemplary eHiFi domains. These ZFN pairs were tested in K562 cells and their nuclease cleavage activities were measured by Cel1 assay and MiSeq sequencing.

Figure 12:
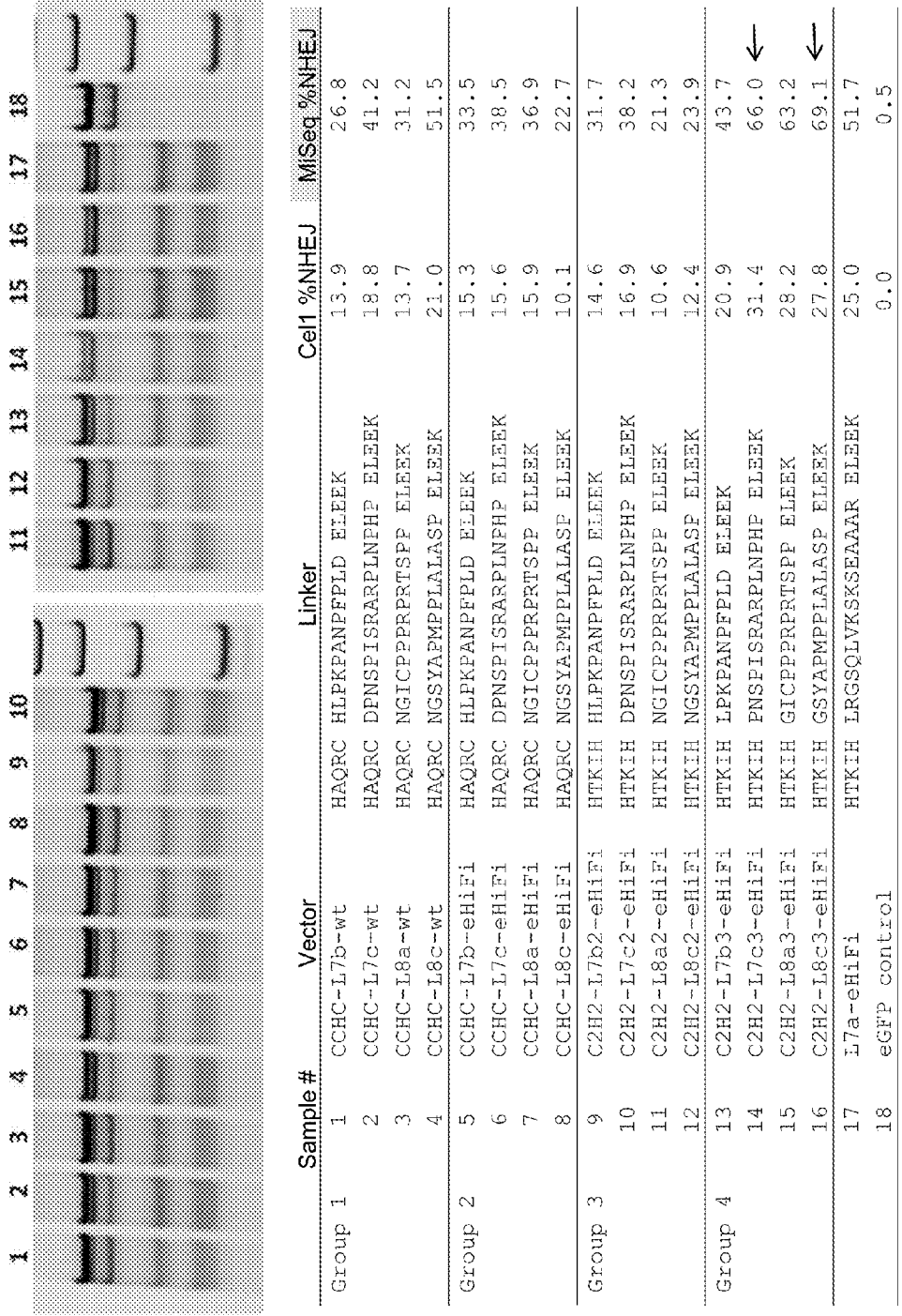
FIG. 12 shows activity, as determined by Cell assay and sequence analysis, of the indicated linkers in the indicated zinc finger and cleavage domain vectors (SEQ ID NOs:258-261, 258-261 and 262-270, respectively, in order of appearance). As shown the linker sequence extends from the amino acid residue immediately C-terminal to the $2^{nd}$ histidine residue of the ZFP sequence to the amino acid residue immediately N-terminal to the EL FokI sequence. Arrows indicate the two most active 7 bp gap linker sequences.

The results, as shown in FIG. 12, demonstrated that (1) these linkers are effective in both wild type and eHiFi FokI architectures (comparing Group 1 and Group 2); (2) these linkers are effective in the context of both C3H and C2H2 architecture (comparing Group 2 and Group 3); and (3) removing one amino acid residue (from the N-terminal) in each linker (shown in Group 3) resulted in significantly higher activity as compared to linkers with the C-terminal residue and, in most instance, as compared to the currently-used L7a linker (sample #17 in FIG. 12).

Subsequently, the two most active 7-bp linker sequences ("L7c3" and "L8c3", indicated by arrows) were modified to make the C-terminus of a ZFP ends with the conventional "HTKIHLRGS" peptide sequence (SEQ ID NO: 50), which allows ZFN assembly using the same process as all other C2H2 ZFNs.

To ensure the modified linkers possessed the same or higher activities than the conventional "L7a" linker on a 7-bp gap site, four linker variants were designed for both "L7c3" and "L8c3" and engineered into two ZFN pairs (see FIG. 13). These ZFNs were tested in human CD34 cells and their NHEJ activities were measured with MiSeq analyses.

As shown in FIG. 13, while all variants tested were active, many of them showed higher activities than the conventional "L7a" bearing ZFNs, including the highest activity as seen with "L7c5" and "L7e4" variants.

Example 6: Optimizing ZFN Activity by Changing the ZFP-FokI Junction Sequences

Figure 14:
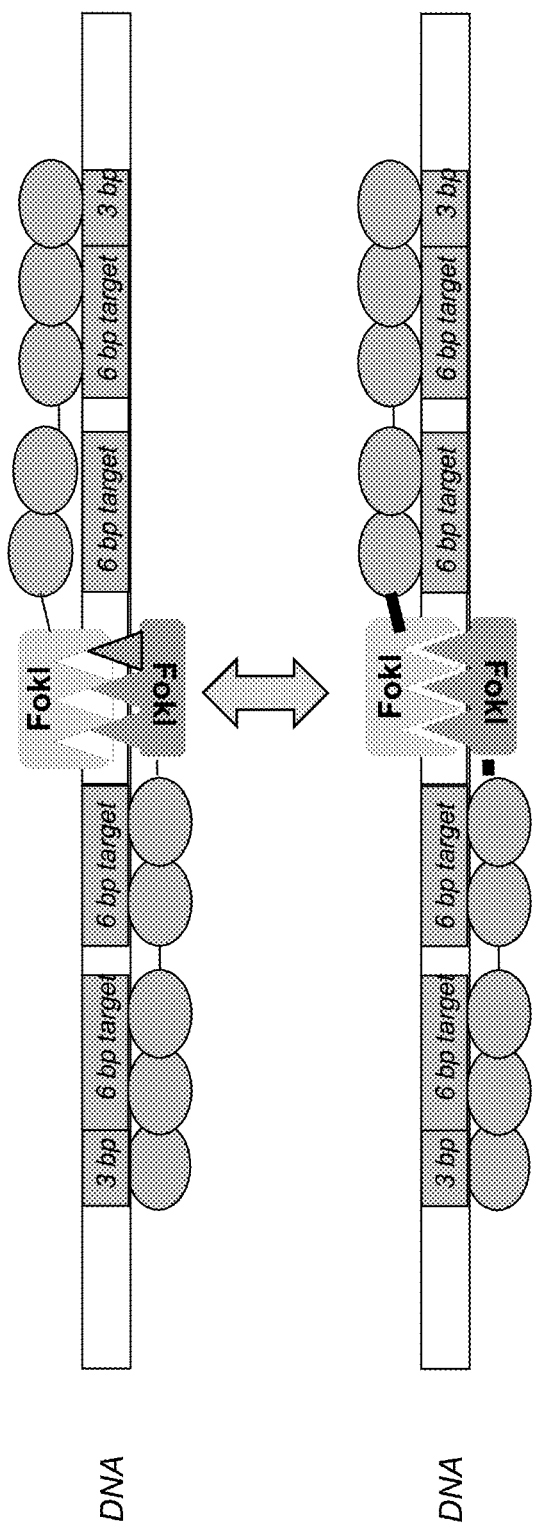
FIG. 14 is a schematic illustrating dimerization (e.g., heterodimerization) of FokI cleavage domains upon binding of ZFNs to their target sites with the indicated gaps.

The conventional junction sequence between ZFP and FokI nuclease domain is "-HTKIHLRGSQLVKSELEEK-" (SEQ ID NO:51). Since ZFN activity can be affected by many factors including the gap length between the two ZFP binding sites and the ZFP affinity to its binding sites, we tested whether the cleavage efficiency of a pair of ZFNs could be modulated by changing the length and/or compositions at the junction sites to optimize the heterodimer interaction between the two FokI cleavage domains. See, FIG. 14. ZFNs of C2H2 or C3H structure can be used.

In particular, a series of 24 junction variants were designed and engineered into a pair of ZFNs target to a 6-bp gap site. See, FIG. 15. Some junction variants have the same length as the conventional one but with different (substituted) amino acid residue(s). In addition, these variants also contain additional amino acids or have some amino acids removed (as shown in FIG. 15).

These ZFNs were tested in K562 cells in the following ways: (1) the 24 left ZFN variants were paired with the right ZFN containing the conventional linker, (b) the 24 right ZFN variants were paired with the left ZFN containing the conventional linker, and (c) the 24 left ZFN variants were paired with each of the right ZFN variants. The ZFN NHEJ activities were measured by MiSeq.

As shown in FIG. 15, ZFN activities were affected by pairing ZFNs containing the various junction linkers. Notably, many of the modified junction regions showed significantly higher NHEJ activities when comparing to the pair of ZFNs containing both of the conventional junction sequences.

Selected junction sequences were also tested using ZFN pairs that target a different site. Two ZFNs pairs with the junction variants were transfected into human HepG2 cells and their NHEJ activities were measured by MiSeq. The data as shown in FIG. 16 demonstrated again that the ZFN activities can be further improved by modulating the ZFP-FokI junction sequences.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A fusion protein comprising
   a DNA-binding domain having an N-terminus and a C-terminus, wherein the DNA-binding domain binds to a nucleotide target site;
   a truncated FokI cleavage domain in which the N-terminal residues QLVKS (residues 158 to 162 of SEQ ID NO:1) are deleted; and
   a linker between the C-terminus of the DNA-binding domain and the N-terminus of the cleavage domain, wherein the linker comprises a sequence selected from the group consisting of (N)GICPPPRPRTSPP (L8a, SEQ ID NO:2); (T)GTAPIEIPPEVYP (L8b, SEQ ID NO:3); (N)GSYAPMPPLALASP (L8c, SEQ ID NO:4); (P)GIYTAPTSRPTVPP (L8d, SEQ ID NO:5); (N)GSQTPKRFQPTHPSA (L8e, SEQ ID NO:6); TGLMPPSHPRQPIHINF (L8g, SEQ ID NO:234); TGTVHTSPICPQTYP (L8i, SEQ ID NO:161); TGSGTPTRPHPPLPP (L8j, SEQ ID NO:235); (H)LPKPANPFPLD (L7-1, SEQ ID NO:7); (H)RDGPRNLPPTSPP (L7-2, SEQ ID NO:8); (H)RLPDSPTALAPDTL (L7-6, SEQ ID NO:9); (D)PNSPISRARPLNPHP (L7-3, SEQ ID NO:10); (Y)GPRPTPRLRCPIDSLIFR (L7-5, SEQ ID NO:11); (H)CPASRPIHP (L6-2, SEQ ID NO:12); (G)LQSLIPQQLL (L6-6, SEQ ID NO:13); (G)LQPTVNHEYNN (L6-7, SEQ ID NO:14); and (P)ANIHSLSSPPPL (L6-1, SEQ ID NO:15) and further wherein the amino acid residue shown in round parentheses is optionally present.

2. The fusion protein of claim 1, wherein the linker further comprises a ZC sequence (SEQ ID NO:35).

3. The fusion protein of claim 2, wherein the ZC sequence is at the N-terminus of the linker.

4. The fusion protein of claim 1, wherein the DNA-binding domain is a zinc finger protein.

5. A dimer comprising two fusion proteins according to claim 1.

6. The dimer of claim 5, wherein the dimer is a homodimer or heterodimer.

7. A polynucleotide encoding at least one fusion protein according to claim 1.

8. A cell comprising a fusion protein according to claim 1.

9. A cell comprising a polynucleotide according to claim 7.

10. A method for targeted cleavage of cellular chromatin in a region of interest in a cell, the method comprising:
    expressing a pair of nucleases in the cell under conditions such that cellular chromatin is cleaved at the region of interest, wherein the nucleases bind to target sites in the region of interest and further wherein at least one nuclease comprises a fusion protein according to claim 1.

11. The method of claim 10, wherein both nucleases comprise fusions proteins according to claim 1.

12. The method of claim 10, wherein the target sites for the zinc finger nucleases are 3 to 20 base pairs apart.

13. The method of claim 10, further comprising the step of introducing a donor polynucleotide into the cell, wherein all or part of the donor polynucleotide is incorporated into the region of interest following cleavage.

14. A kit for producing a nuclease, the kit comprising a fusion protein according to claim 1 contained in one or more containers, optional hardware, and instructions for use of the kit.

15. A kit for producing a nuclease, the kit comprising a polynucleotide according to claim 7 contained in one or more containers, optional hardware, and instructions for use of the kit.

16. The kit of claim 14, further comprising a donor polynucleotide.

* * * * *